(12) United States Patent
Takaichi

(10) Patent No.: US 11,612,369 B2
(45) Date of Patent: Mar. 28, 2023

(54) COMMUNICATION APPARATUS, AND MEDICAL APPARATUS

(71) Applicant: General Electric Company, Schenectady, NY (US)

(72) Inventor: Yoshio Takaichi, Tokyo (JP)

(73) Assignee: General Electric Company, Schenectady, NY (US)

( * ) Notice: Subject to any disclaimer, the term of this patent is extended or adjusted under 35 U.S.C. 154(b) by 313 days.

(21) Appl. No.: 16/852,855

(22) Filed: Apr. 20, 2020

(65) Prior Publication Data

US 2020/0337657 A1 Oct. 29, 2020

(30) Foreign Application Priority Data

Apr. 26, 2019 (JP) .............................. JP2019-085738

(51) Int. Cl.
*H04R 3/00* (2006.01)
*H04R 29/00* (2006.01)
(Continued)

(52) U.S. Cl.
CPC ................ *A61B 6/46* (2013.01); *A61B 6/032* (2013.01); *A61B 6/4078* (2013.01);
(Continued)

(58) Field of Classification Search
CPC . H04R 3/00; H04R 3/005; H04R 3/04; H04R 3/12; H04R 29/00; H04R 29/001;
(Continued)

(56) References Cited

U.S. PATENT DOCUMENTS 3,943,356 A * 3/1976 Schmutzer ............... H05G 1/66
378/94
4,620,313 A * 10/1986 Erker ..................... A61B 6/032
378/19
(Continued)

FOREIGN PATENT DOCUMENTS

AU 2015200573 A1 * 8/2015 ......... A61B 5/04017
CN 105051810 A * 11/2015 ........... G10K 11/178
(Continued)

OTHER PUBLICATIONS

Japanese Application No. 2019-085738 filed Apr. 26, 2019—Notice of Preliminary Rejection dated Apr. 28, 2020; 2 pages.

*Primary Examiner* — Thang V Tran

(57) ABSTRACT

[Problem] To provide a communication apparatus that makes a subject's voice more audible.
[Means for Solution]
A communication apparatus 60 has: a microphone 61 for receiving, during rotation of a rotating section 26, sound containing a voice of a subject 5 to be examined and noise caused by the rotation of the rotating section 26; a DSP 623 for executing filter processing for reducing said noise contained in the sound received by the microphone 61, wherein the DSP 623 determines a frequency of the noise caused by the rotation of the rotating section 26 based on a rotational speed vi of the rotating section 26, and sets a filter characteristic F(ti) for the DSP so that a frequency component of the noise contained in the sound is removed; and a speaker 63 for outputting the sound which contains the voice of the subject 5 and from which the frequency component of said noise has been removed.

13 Claims, 15 Drawing Sheets

(51) Int. Cl.
*A61B 6/03* (2006.01)
*A61B 6/00* (2006.01)
*G10L 25/51* (2013.01)
*G10L 21/0232* (2013.01)
G10L 21/0216 (2013.01)
H03F 3/183 (2006.01)

(52) U.S. Cl.
CPC .......... *A61B 6/4085* (2013.01); *A61B 6/4452* (2013.01); *G10L 21/0232* (2013.01); *G10L 25/51* (2013.01); *H04R 29/001* (2013.01); G10L 2021/02163 (2013.01); H03F 3/183 (2013.01); H03F 2200/03 (2013.01); H04R 3/00 (2013.01)

(58) Field of Classification Search
CPC ......... H04R 29/004; A61B 6/03; A61B 6/032; A61B 6/035; A61B 6/44; A61B 6/4429; A61B 6/4435; A61B 6/4452; A61B 6/4078; A61B 6/4085; A61B 6/46; A61B 6/54; A61B 6/527; A61B 6/547; A61B 6/5264; G10L 25/48; G10L 25/51; G10L 21/0232; G10L 2021/02163; H03F 3/183; H03F 2200/03

See application file for complete search history.

(56) References Cited

U.S. PATENT DOCUMENTS

| | | | |
|---|---|---|---|
| 6,553,091 B2* | 4/2003 | Takanashi | A61B 6/035 378/207 |
| 2005/0220382 A1 | 10/2005 | Katou | |
| 2006/0034472 A1 | 2/2006 | Bazarjani | |
| 2015/0117596 A1* | 4/2015 | Cao | A61B 6/5264 378/20 |
| 2019/0088244 A1* | 3/2019 | Goto | B64C 27/001 |
| 2019/0150878 A1* | 5/2019 | Smith | A61B 6/5205 |
| 2020/0036305 A1* | 1/2020 | John | B64C 39/024 |

FOREIGN PATENT DOCUMENTS

| | | | |
|---|---|---|---|
| JP | 2001299735 A | | 10/2001 |
| JP | 2002224079 A | * | 8/2002 |
| JP | 2004141534 A | * | 5/2004 |
| JP | 2015033437 A | * | 2/2015 |

* cited by examiner

FIG. 7
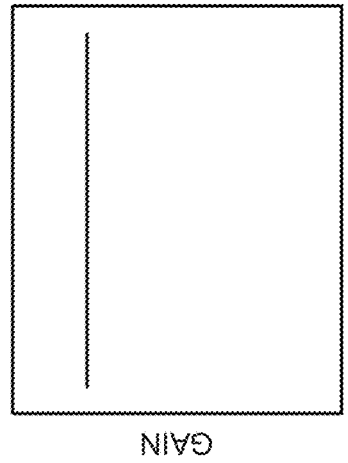
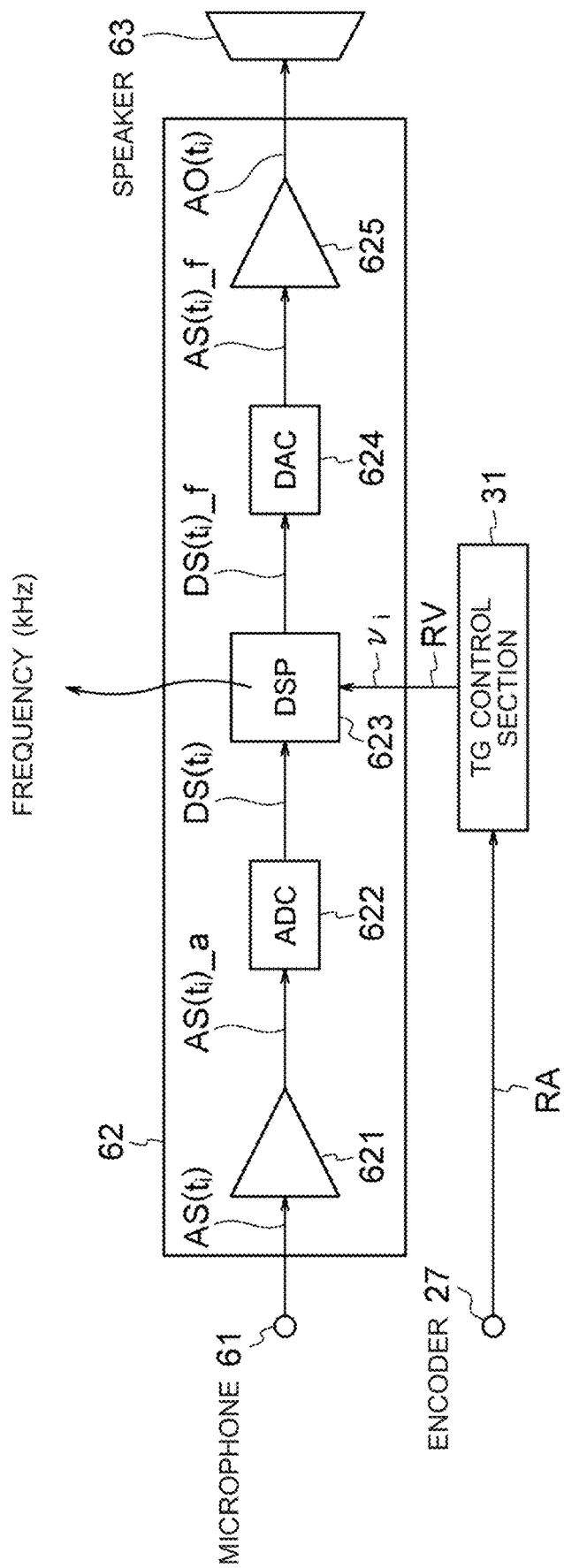

FIG. 14
SOUND SPECTRUM SP BEFORE BEING FILTER-PROCESSED
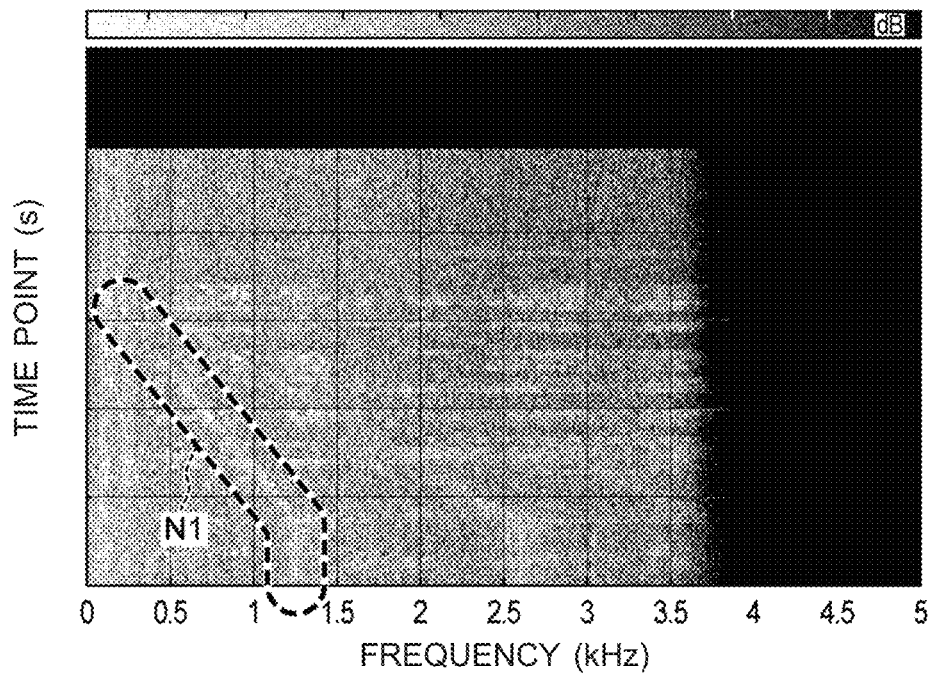
SOUND SPECTRUM SP AFTER BEING FILTER-PROCESSED
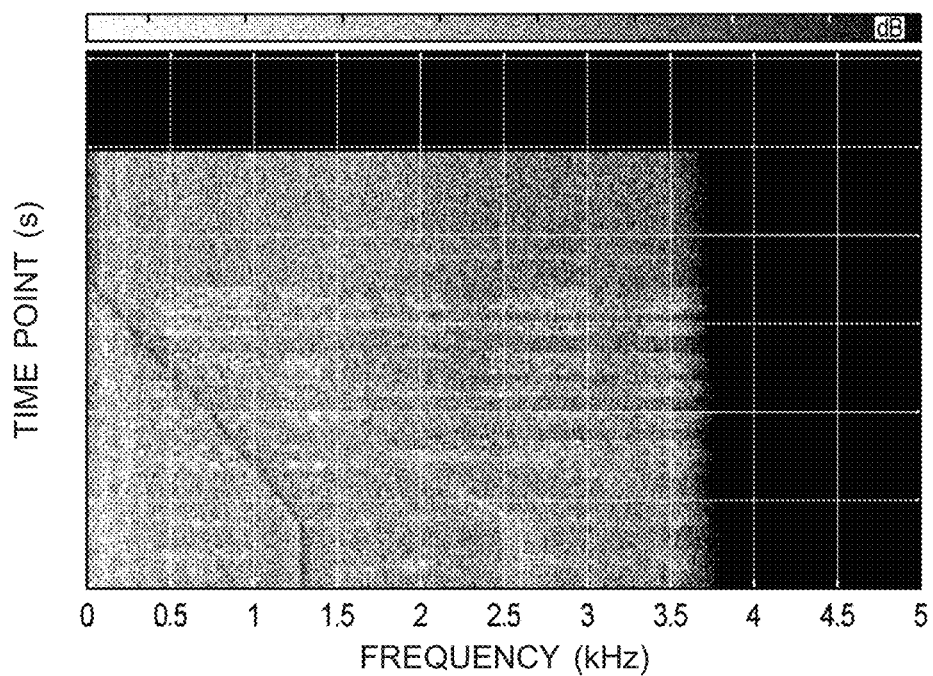

COMMUNICATION APPARATUS, AND MEDICAL APPARATUS

CROSS-REFERENCE TO RELATED APPLICATIONS

This specification is based upon and claims the benefit of priority from United Kingdom patent application number GB 1820116.0 filed on Dec. 11, 2018, the entire contents of which are incorporated herein by reference.

FIELD OF THE INVENTION

The present invention relates to a communication apparatus for communicating a voice of a subject to be examined to an operator, and a medical apparatus having the communication apparatus.

BACKGROUND

As apparatuses for acquiring an image of the inside of a subject to be examined, CT (Computed Tomography) apparatuses are known. The CT apparatuses have the merit as compared with MRI (Magnetic Resonance Imaging) apparatuses in the fact that their scan time is generally shorter and therefore they can reduce the stress on the subject, and thus the CT apparatuses are introduced in various medical facilities, such as hospitals.

A CT apparatus has a gantry and a table as its main components. The gantry and table are placed in a scan room. The gantry is provided with a rotating section incorporating therein an X-ray tube and a detector. In imaging a subject, a scan is performed while rotating the rotating section. The CT apparatus also has an operation console for operating the gantry and table, and the operation console is placed in an operation room provided separately from the scan room. The operator can control the gantry and table by operating the operation console placed in the operation room.

The CT apparatus moreover has a communication apparatus for enabling the subject to transmit his/her voice to the operator during his/her imaging. The communication apparatus has a microphone for receiving the subject's voice, and a speaker for transmitting the voice received by the microphone to the operator working at the operation console. Once the subject has made a voice during imaging, the microphone receives the subject's voice, and thus, the subject's voice is emitted from the speaker. Therefore, the operator can hear the subject's voice from the speaker while working at the operation console.

However, when the rotating section of the gantry rotates, noise is generated. Therefore, the microphone receives the noise in addition to the subject's voice, so that the speaker outputs sound of the subject's voice mixed with the noise. This poses a problem that the subject's voice becomes difficult to hear. Accordingly, an example of a communication apparatus for addressing the problem is disclosed in Patent Document 1.

PRIOR-ART REFERENCE

Patent Document

[Patent Document 1] Japanese Patent Application KOKAI No. 2000-070256

SUMMARY OF THE INVENTION

Problem to be Solved by the Invention

According to Patent Document 1, there is disclosed an approach comprising classifying states of a scanner/gantry unit 1 into four, i.e., a standby state, an activating state, a scan state, and a decelerating state, storing parameters representing unwanted noise for each of the states, and controlling a DSP according to the state of the unit 1. The DSP applies filter processing to sound input from a microphone depending upon the parameters to thereby remove noise contained in the sound input from the microphone.

The frequency characteristics of the noise, however, vary depending upon the rotational speed of the rotating section incorporated in the gantry. Therefore, the communication apparatus according to Patent Document 1 has a problem that noise cannot fully be reduced because the apparatus cannot handle the variation of the rotational speed of the rotating section.

Moreover, the CT apparatus also comprises, in addition to the rotating section incorporating therein an X-ray tube and a detector, a rotating section for rotating an anode of the X-ray tube, a rotating section used for a cooling mechanism, and the like, which may become causes of noise.

Furthermore, a medical apparatus, such as the CT apparatus, generally comprises a rotating section for driving a support mechanism (for example, the table) for supporting the subject, and the like, which may also become causes of noise.

Therefore, there is a need for a communication apparatus in which an influence of noise is mitigated and which is capable of making a subject's voice more audible, and a medical apparatus comprising the communication apparatus.

Means for Solving the Problem

The present invention, in its first aspect, is a communication apparatus used in a medical apparatus comprising a rotating section, said communication apparatus having:

a microphone for receiving, during rotation of said rotating section, sound containing a voice of a subject to be examined and noise caused by the rotation of said rotating section;

a filter section for executing filter processing for reducing said noise contained in the sound received by said microphone, wherein said filter section determines a frequency of the noise caused by the rotation of said rotating section based on a rotational speed of said rotating section, and sets a filter characteristic for said filter section so that a frequency component of said noise contained in said sound is removed; and a speaker for outputting the sound from which the frequency component of said noise has been removed.

The present invention, in its second aspect, is a medical apparatus having the communication apparatus as described regarding the first aspect.

The present invention, in its third aspect, is a program applied to a communication apparatus having a microphone for receiving, during rotation of a rotating section provided in a medical apparatus, sound containing a voice of a subject to be examined and noise caused by the rotation of said rotating section; a filter section for executing filter processing for reducing said noise contained in the sound received by said microphone; and a speaker for outputting the sound from which said noise has been reduced, said program being for causing said filter section to execute:

determination of a frequency of the noise caused by the rotation of said rotating section based on a rotational speed of said rotating section; and setting of a filter characteristic for said filter section so that a frequency component of said noise contained in said sound is removed.

The present invention, in its fourth aspect, is a non-transitory computer-readable storage medium storing one or more processor-executable instructions wherein said one or more instructions, when executed by said processor, causes acts to be performed comprising:

receiving a signal representing a rotational speed of said rotating section;

determining, based on said signal, a frequency of noise caused by rotation of said rotating section; and setting a filter characteristic for said filter section so that a frequency component of said noise contained in said sound is removed.

Effect of the Invention

The communication apparatus determines, based on the rotational speed of the rotating section, a frequency of noise caused by rotation of the rotating section. Therefore, the filter characteristic may be changed according to the noise characteristic varying depending upon the rotational speed of the rotating section, so that even when the rotational speed of the rotating section changes, a subject's voice having a reduced influence of noise can be output from the speaker.

BRIEF DESCRIPTION OF THE DRAWINGS

FIG. 7 An explanatory diagram for an action of the intercom board 60 at time point t1≤ti<t8.

FIG. 14 A diagram showing a sound spectrum SP' after being filter-processed by a DSP.

EMBODIMENTS FOR CARRYING OUT THE INVENTION

Now embodiments for carrying out the invention will be described, although the present invention is not limited thereto.

(1) First Embodiment

Figure 1:
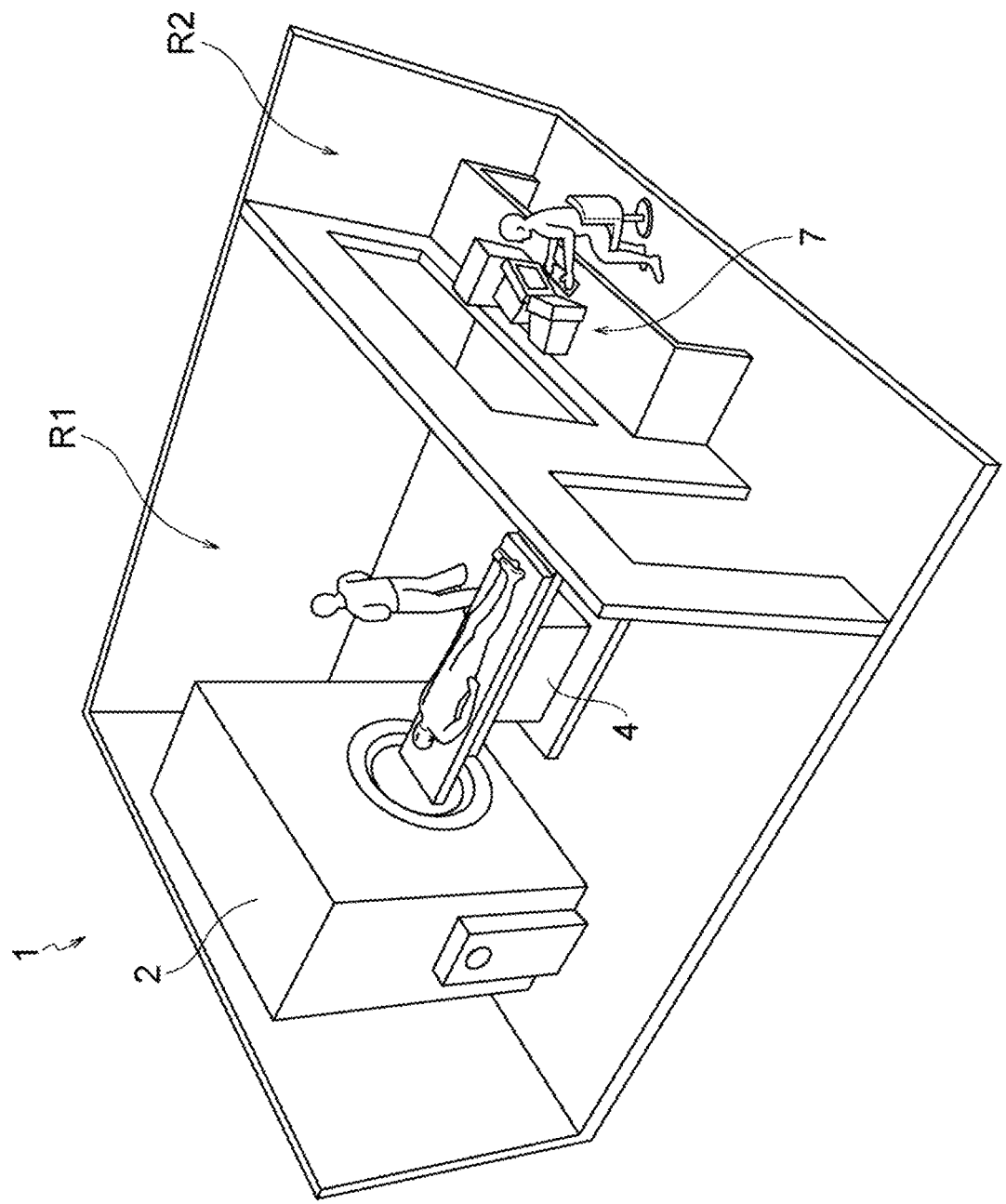
FIG. 1 An external view of an X-ray CT apparatus in a first embodiment.

FIG. 1 is an external view of an X-ray CT apparatus in a first embodiment.

As shown in FIG. 1, the X-ray CT apparatus 1 comprises a gantry 2, a table 4, and an operation console 7.

The gantry 2 and table 4 are placed in a scan room R1. The operation console 7 is placed in an operation room R2 different from the scan room R1.

Figure 2:
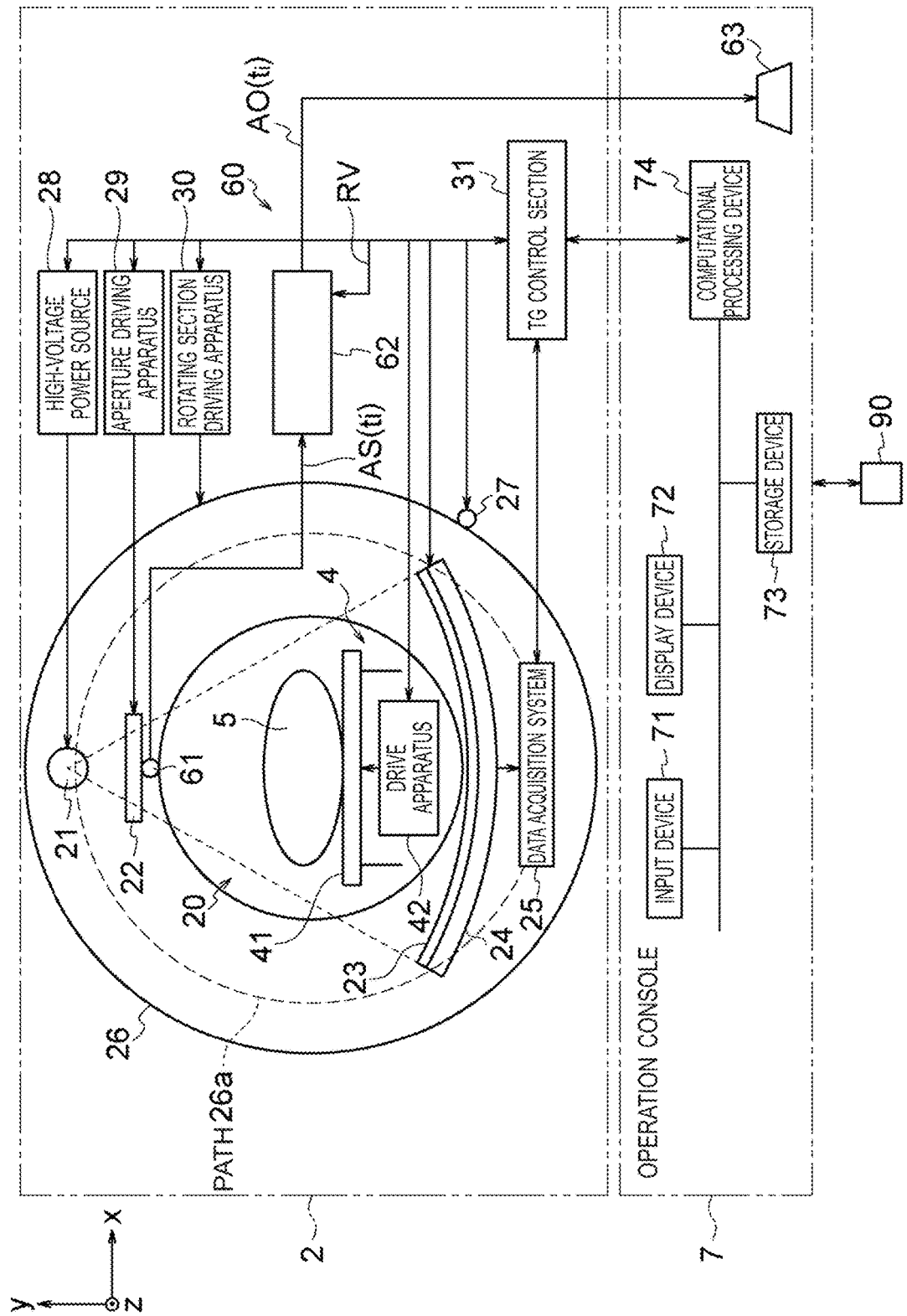
FIG. 2 A diagram schematically showing a hardware configuration of the X-ray CT apparatus 1 in accordance with the first embodiment.

FIG. 2 is a diagram schematically showing a hardware configuration of the X-ray CT apparatus 1 in accordance with the first embodiment.

The gantry 2 has a bore portion 20 into which a subject 5 to be examined is carried.

The gantry 2 also has an X-ray tube 21, an aperture 22, a collimator device 23, an X-ray detector 24, a data acquisition system 25, a rotating section 26, an encoder 27, a high-voltage power source 28, an aperture drive apparatus 29, a rotation drive apparatus 30, a TG (Gantry Table) control section 31, and the like.

The rotating section 26 is configured to be rotatable along a path 26a surrounding the bore portion 20 in a plane (xy-plane) orthogonal to a subject's body axis (z-axis direction). The rotating section 26 is provided in its proximity with the encoder 27 for detecting a rotation angle of the rotating section 26.

The X-ray tube 21, aperture 22, collimator device 23, X-ray detector 24, and data acquisition system 25 are mounted on the rotating section 26.

The X-ray tube 21 and X-ray detector 24 are placed facing each other sandwiching therebetween the bore portion 20 of the gantry 2.

The aperture 22 is placed between the X-ray tube 21 and bore portion 20. The aperture 22 shapes X-rays emitted from an X-ray focus of the X-ray tube 21 toward the X-ray detector 24 into a fan beam or a cone beam.

The collimator device 23 is placed between the bore portion 20 and X-ray detector 24. The collimator device 23 removes scatter rays entering the X-ray detector 24.

The X-ray detector 24 has a plurality of X-ray detector elements two-dimensionally arranged in directions of the extent and the thickness of the fan-shaped X-ray beam emitted from the X-ray tube 21. Respective X-ray detector elements detect X-rays passing through the subject 5, and output electric signals depending upon the intensity of the X-rays.

The data acquisition system 25 receives the electric signals output from the X-ray detector elements in the X-ray detector 24, and converts them into X-ray data for acquisition.

The table 4 has a cradle 41 and a drive apparatus 42. The subject 5 is laid on the cradle 41. The drive apparatus 42 drives the table 4 and cradle 41 so that the cradle 41 can be moved in y- and z-directions.

The high-voltage power source 28 supplies high voltage and current to the X-ray tube 21.

The aperture drive apparatus 29 drives the aperture 22 and deforms its opening.

The rotation drive apparatus 30 rotationally drives the rotating section 26. The rotation drive apparatus 30 may comprise, for example, a motor and a transmission mechanism for transmitting power the motor generates to the rotating section 26. The transmission mechanism may be constructed using a belt and gears, for example.

The TG control section 31 executes processing for controlling several apparatuses and sections in the gantry 2, the drive apparatus 42, and the like. For example, the TG control section 31 receives an angle signal representing an angle of the rotating section 26 from the encoder 27, calculates a rotational speed of the rotating section 26 based on the received angle signal, and outputs a signal RV representing the calculated rotational speed to a DSP 623 (see FIG. 3) in an intercom board 62 discussed later. The TG control section 31 comprises a processor for receiving the angle signal, calculating the rotational speed of the rotating section, and outputting the signal RV representing the rotational speed to the DSP 623.

Programs for causing the TG control section 31 to execute these processing may be stored in a storage section (not shown) provided in the TG control section 31. The TG control section 31 executes the processing by loading the programs stored in the storage section.

The operation console 7 accepts several kinds of operations from an operator. The operation console 7 has an input device 71, a display device 72, a storage device 73, and a computational processing device 74.

The input device 71 is configured to comprise buttons, a keyboard, and the like for accepting an input of a command and information from the operator, and to further comprise a pointing device, and the like. The display device 72 is an LCD (Liquid Crystal Display), an organic EL (Electro-Luminescence) display, or the like.

The storage device 73 is an HDD (Hard Disk Drive), semiconductor memory such as RAM (Random Access Memory), ROM (Read Only Memory), and the like. The operation console 7 may have all of the HDD, RAM and ROM as the storage device 73. Moreover, the storage device 73 may comprise a portable storage medium, such as a CD (Compact Disk), a DVD (Digital Versatile Disk), and the like.

The computational processing device 74 is an apparatus for executing several kinds of computation, and may be constructed using a processor.

The CT apparatus 1 moreover has a communication apparatus 60 for enabling the operator to hear a voice made by the subject 5.

The communication apparatus 60 has a microphone 61, an intercom board 62, and a speaker 63.

The microphone 61 is for receiving a subject's voice, and is placed in the proximity of the bore portion 20 of the gantry 2. The microphone 61 outputs a signal AS(ti) representing sound received at time point ti to the intercom board 62. The signal AS(ti) is an analog signal. Here, a subscript 'i' in time point ti is used to express a difference among time points t1 through t24 discussed later (see FIG. 4, for example), where a smaller value of i represents a temporally earlier time point, while a larger value of i represents a temporally later time point. For example, comparing time point t1 (that is, i=1) with time point t2 (that is, i=2), time point t1 represents a time point temporally earlier than time point t2.

The intercom board 62 receives the signal AS(ti) from the microphone 61, and processes the received signal AS(ti). The processed signal AS(ti) is output to the speaker 63 as an output signal AO(ti) at time point ti.

The speaker 63 receives the signal AO(ti) from the intercom board 62, and outputs sound according to the received signal AO(ti).

Figure 3:
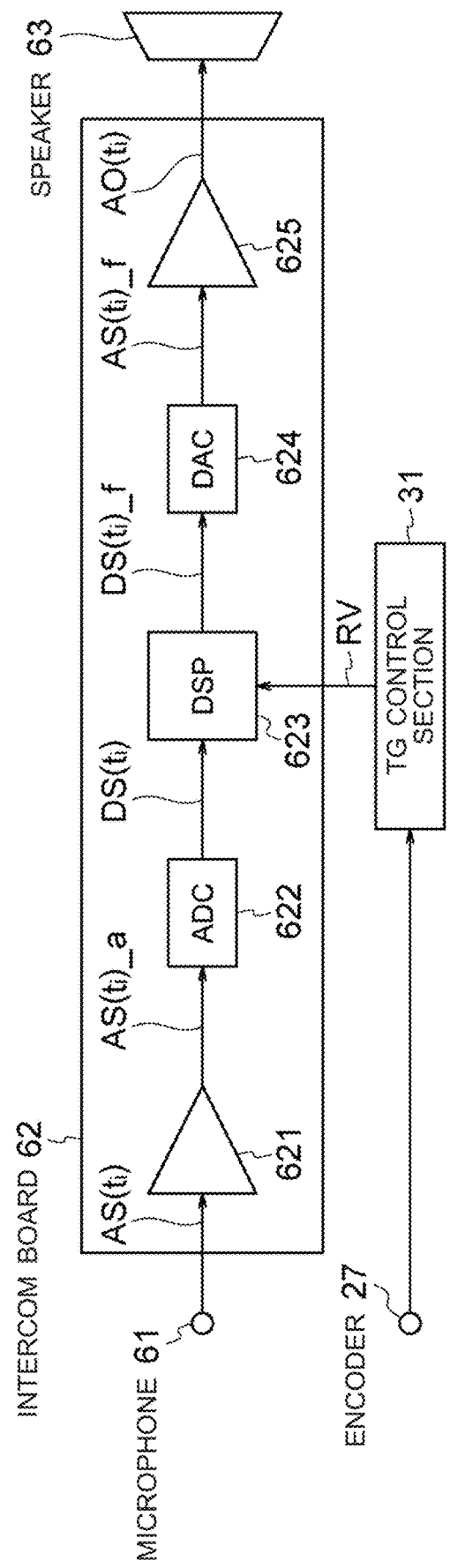
FIG. 3 A block diagram of an intercom board 62.

FIG. 3 is a block diagram of the intercom board 62.

The intercom board 62 has a preamplifier 621, an ADC (Analog-to-Digital Converter) 622, a DSP (Digital Signal Processor) 623, a DAC (Digital-to-Analog Converter) 624, and a speaker amplifier 625.

The preamplifier 621 amplifies the analog signal AS(ti) representing sound received from the microphone 61, and outputs an amplified analog signal AS(ti)_a to the ADC 622.

The ADC 622 converts the analog signal AS(ti)_a received from the preamplifier 621 into a digital signal DS(ti).

The DSP 623 receives the digital signal DS(ti) from the ADC 622, and further, receives a signal RV representing the rotational speed of the rotating section 26 from the TG control section 31. The DSP 623 is a filter section for performing filter processing for reducing the frequency of noise contained in the digital signal DS(ti) based on the received signal RV.

The CT apparatus 1 has a non-transitory computer-readable storage medium storing one or more instructions for causing the DSP 623 to perform the following acts (a) to (c):

(a) receiving the signal RV representing the rotational speed of the rotating section 26;

(b) determining, based on the signal RV, a frequency of noise caused by rotation of the rotating section 26; and (c) setting the filter characteristic for the DSP 623 so that a frequency component of the noise contained in the sound received at the microphone 61 is removed.

The intercom board 62 comprises a non-transitory computer-readable storage medium (not shown) storing one or more instructions for causing the acts (a) to (c) to be performed, and a processor (not shown) for executing the instructions stored in the storage medium. Note that the aforementioned non-transitory, computer-readable storage medium and processor may be provided in any other circuitry (the TG control section 31, for example) than the intercom board 62.

The DSP 623 outputs a filter-processed digital signal DS(ti)_f.

The DAC 624 converts the digital signal DS(ti)_f received from the DSP 623 into an analog signal AS(ti)_f.

The speaker amplifier 625 amplifies the analog signal AS(ti)_f, and outputs the amplified analog signal to the speaker 63 as an output signal AO(ti).

The intercom board 62 is configured as described above.

The speaker 63 receives the output signal AO(ti) output from the intercom board 62, and outputs sound according to the received signal AO(ti). The speaker 63 is included in the operation console 7. Therefore, the operator staying in the operation room R2 is capable of communicate with the subject 5 staying in the scan room R1 via the communication apparatus 60.

However, when the rotating section 26 of the gantry 2 rotates, noise is generated. Causes of the noise may include, for example, vibrational noise, wind noise, and/or the like caused by rotation of the rotating section 26. Therefore, the microphone 61 receives the noise caused by rotation of the rotating section 26, in addition to the subject's voice. The noise is one of principal causes that make a voice of the subject 5 less audible for the operator. Accordingly, the communication apparatus 60 in the present embodiment is configured to reduce, from the sound received at the microphone 61, the noise caused by rotation of the rotating section 26 of the gantry 2, and to be able to output from the speaker 63 a high-quality voice having a reduced influence of the noise.

Now how the communication apparatus 60 reduces the noise from rotation of the rotating section 26 will be described referring to FIGS. 4 to 13.

Figure 4:
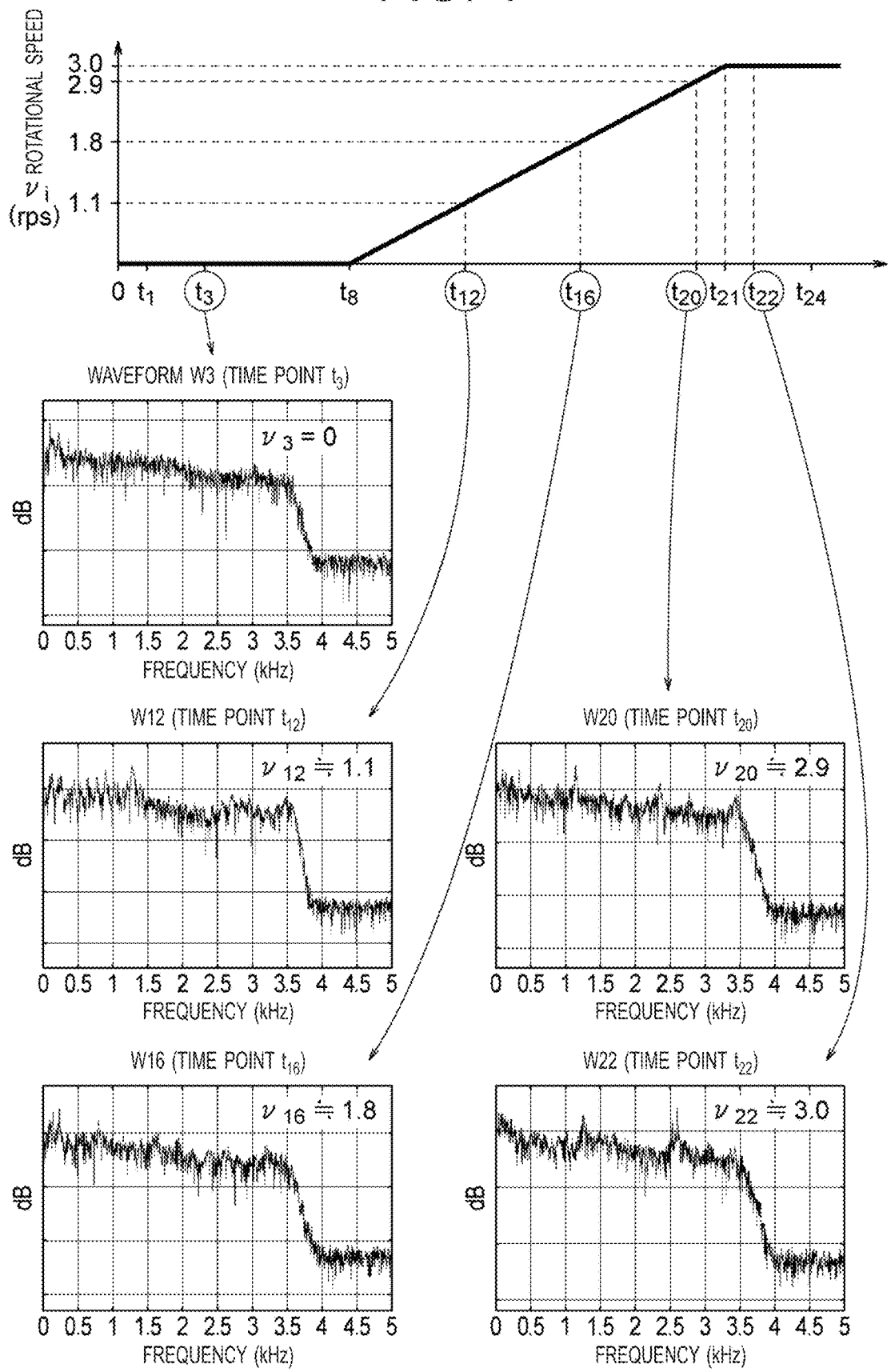
FIG. 4 A diagram showing waveforms obtained from recorded data.

FIG. 4 is a diagram showing waveforms of the sound pressure which is determined from recorded data, wherein the recorded data is obtained by recording noise generated from the CT apparatus 1 while actually rotating the rotating section 26 of the CT apparatus 1.

In the case that the CT apparatus 1 is provided with a recording device, noise can be recorded by the recording device in the CT apparatus 1. In the case that the CT apparatus 1 is provided with no recording device, a recordable device separate from the CT apparatus 1 may be prepared and noise may be recorded using the device.

In FIG. 4 in its upper portion is shown a graph representing a temporal change of the rotational speed of the rotating element 26 while noise is being recorded.

At time point $t1 \leq ti < t8$, the rotating section 26 is in a standstill state. Therefore, the rotational speed vi at time point $t1 \leq ti < t8$ is vi=0 (rps). Here, rps is a unit representing how many rotations the rotating section 26 makes during one second, that is, "revolutions per second."

On the other hand, at time point $t8 \leq ti \leq t24$, the rotating section 26 is in a rotating state. In a period between time points $t8 \leq ti < t21$, the rotating section 26 is controlled so that the speed of the rotating section 26 linearly increases. On the other hand, in a period between time points $t21 \leq ti \leq t24$, the rotating section 26 is controlled so that the rotational speed of the rotating section 26 is constant. Here are shown exemplary rotational speeds v12, v16, v20, and v22 at time points t12, t16, t20, and t22 as representatives of time points $t8 \leq ti \leq t24$. They are $v12 \approx 1.1$ (rps), $v16 \approx 1.8$ (rps), $v20 \approx 2.9$ (rps), and $v22 \approx 3.0$ (rps).

Below the graph are shown waveforms w3, w12, w16, w20, and w22 of the sound pressure obtained at time points t3, t12, t16, t20, and t22 as representatives of time points $t1 \leq ti \leq t24$. The horizontal axis for each waveform is in frequency (kHz), and the vertical axis in sound pressure (dB).

Figure 5:
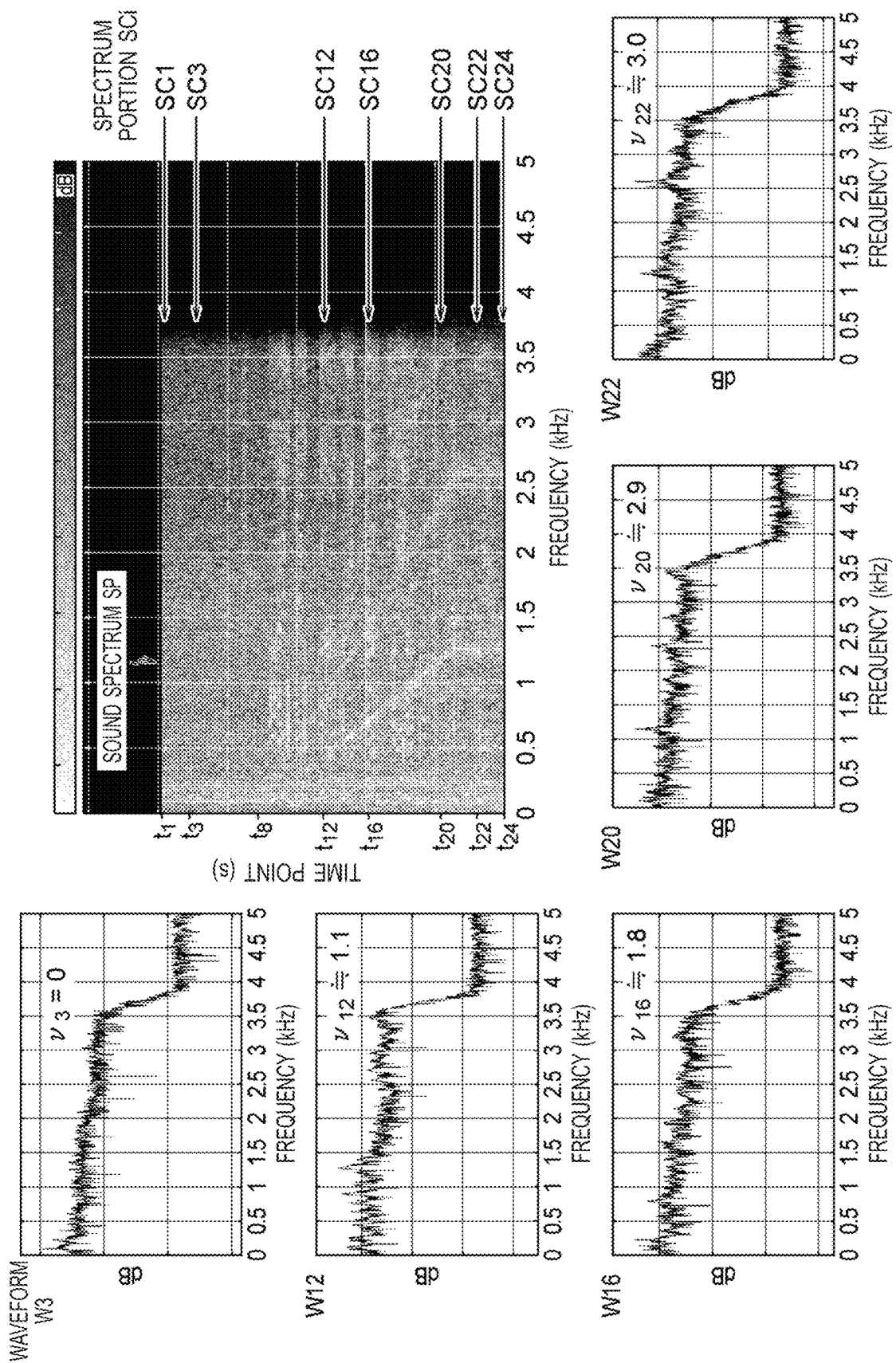
FIG. 5 A diagram showing a sound spectrum SP.

These waveforms are used to create a sound spectrum (see FIG. 5).

FIG. 5 is a diagram showing a sound spectrum SP.

The sound spectrum SP is comprised of spectrum portions SCi ($1 \leq i \leq 24$). A spectrum portion SCi represents a frequency characteristic of the sound pressure of a waveform wi at time point ti. In FIG. 5 are shown waveforms w3, w12, w16, w20, and w22 at time points t3, t12, t16, t20, and t22 as representatives of time points $t1 \leq ti \leq t24$. For example, i=16, that is, a spectrum portion SC16 represents a frequency characteristic of the sound pressure of the waveform w16 at time point t16.

In the sound spectrum SP in FIG. 5, a difference in sound pressure is expressed by grayscale. Specifically, a difference in sound pressure in the sound spectrum SP is expressed by grayscale so that a smaller sound pressure is shown blacker and a larger sound pressure is shown whiter. Now the grayscale in the sound spectrum SP will be described referring to FIG. 6.

Figure 6:
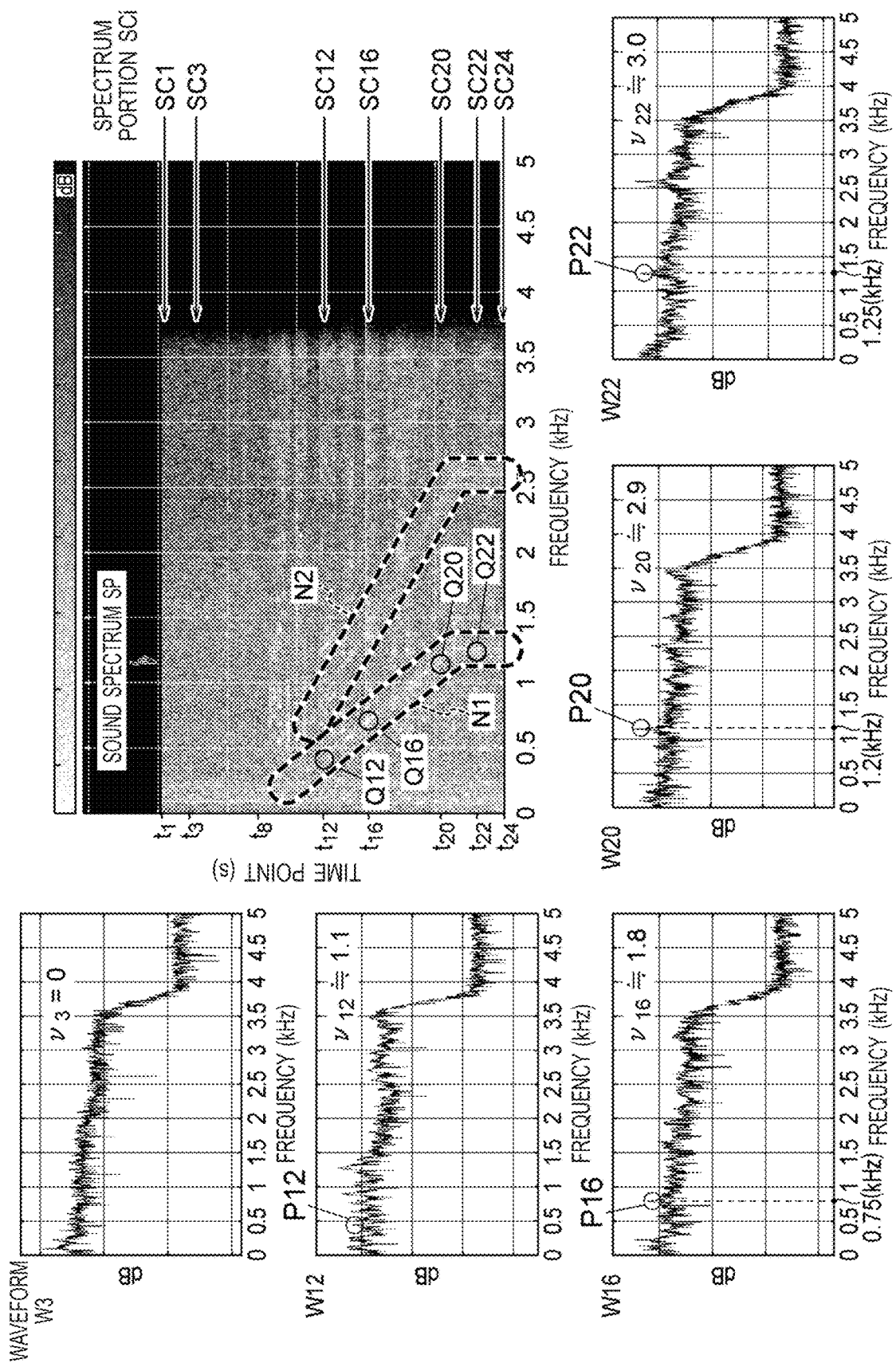
FIG. 6 An explanatory diagram for the grayscale in the sound spectrum SP.

FIG. 6 is an explanatory diagram for the grayscale in the sound spectrum SP. In FIG. 6, in addition to the sound spectrum SP, dashed lines and symbols (N1, N2, Q12, Q16, Q20, Q22) used for explanation are added. Now the grayscale in the sound spectrum SP will be described referring to the waveforms w12, w16, w20, and w22 at time points t12, t16, t20, and t22.

Referring to the waveform w12 at time point t12, a peak P12 of the sound pressure appears in the proximity of frequency f=0.5 kHz in the waveform w12. Therefore, referring to the spectrum portion SC12 of the sound spectrum SP at time point t12, point Q12 lying in the proximity of frequency f=0.5 kHz in the spectrum portion SC12 is expressed in a color close to white for indicating the peak P12 of the sound pressure in the waveform w12.

Next, the waveform w16 at time point t16 will be described.

Referring to the waveform w16 at time point t16, a peak P16 of the sound pressure appears in the proximity of frequency f=0.75 kHz in the waveform w16. Therefore, referring to the spectrum portion SC16 of the sound spectrum SP at time point t16, point Q16 lying in the proximity of frequency f=0.75 kHz in the spectrum portion SC16 is expressed in a color close to white for indicating the peak P16 of the sound pressure in the waveform w16.

Next, the waveform w20 at time point t20 will be described.

Referring to the waveform w20 at time point t20, a peak P20 of the sound pressure appears in the proximity of frequency f=1.2 kHz in the waveform w20. Therefore, referring to the spectrum portion SC20 of the sound spectrum SP at time point t20, point Q20 lying in the proximity of frequency f=1.2 kHz in the spectrum portion SC20 is expressed in a color close to white for indicating the peak P20 of the sound pressure in the waveform w20.

Next, the waveform w22 at time point t22 will be described.

Referring to the waveform w22 at time point t22, a peak P22 of the sound pressure appears in the proximity of frequency f=1.25 kHz in the waveform w22. Therefore, referring to the spectrum portion SC22 of the sound spectrum SP at time point t22, point Q22 lying in the proximity of frequency f=1.25 kHz in the spectrum portion SC22 is expressed in a color close to white for indicating the peak P22 of the sound pressure in the waveform w22.

While the grayscale at points Q12, Q16, Q20, and Q22 in the sound spectrum SP has been explained in the description above, other points in the sound spectrum SP are also expressed in grayscale according to the sound pressure in the waveform.

At time point $t1 \leq ti < t8$, the rotating section 26 is not rotating yet, and therefore, no peak of noise by rotation of the rotating section 26 appears. However, once the rotating section 26 has started rotating, noise by rotation of the rotating section 26 is generated. Therefore, while the rotating section 26 is rotating (time point $t8 \leq ti \leq t24$), a noise profile representing the frequency characteristic due to the noise by rotation of the rotating section 26 appears in the sound spectrum SP.

For example, referring to a noise profile N1 traversing points Q12, Q16, Q20, and Q22, there is shown a case that, in a period between time points $t8 \leq ti < t21$, the peak of the sound pressure due to noise linearly shifts with time in a direction of a larger frequency, while in a period between time points $t21 \leq ti \leq t24$, the peak of the sound pressure appears at a specific frequency ($\approx 1.25$ kHz).

It should be noted that noise profiles other than the noise profile N1 also appear. For example, on the right side of the noise profile N1 appears a noise profile N2. The noise profile N2 has relatively smaller a sound pressure than the noise profile N1, but the peak of the sound pressure in the noise profile N2 linearly shifts in a direction of a larger frequency with an increase of the rotational speed of the rotating section 26, similarly to the noise profile N1.

As described earlier, the inventor of the present application focuses upon the frequency characteristics of noise appearing in a sound spectrum SP, and as a result, has discovered that a generally linear relationship holds between the rotational speed of the rotating section 26 and the peak of the frequency of noise. For example, in the noise profile N1, representing the rotational speed of the rotating section 26 at time point ti as vi, and the frequency of noise generated while the rotating section 26 is rotating at a rotational speed vi as f1(vi), the relationship between f1(vi) and vi can be expressed by EQ. (1) below:

$$f1(vi)=k1*vi, \quad (1)$$

where k1: constant.

The constant k1 corresponds to a slope of the noise profile N1 appearing in the sound spectrum SP. In the case that the noise profile N1 exhibits the slope shown in FIG. 6, the value of k1 may be calculated as k1≈0.42. Therefore, given k1=0.42, a frequency f1(vi) may be expressed by EQ. (2) below:

$$f1(vi)=0.42*vi. \quad (2)$$

The other noise profile N2 can also be expressed by a simple linear relationship, similarly to the noise profile N1.

Therefore, given a known rotational speed vi of the rotating section 26, the frequency of noise caused by rotation of the rotating section 26 can be estimated, which makes it possible to identify the frequency of noise due to rotation of the rotating section 26 from among frequencies contained in the sound received at the microphone 61. Given the identified frequency of noise, noise caused by rotation of the rotating section 26 may be removed from the sound received at the microphone 61, and thus, even in the case that noise is generated by rotation of the rotating section 26 while the subject 5 is making a voice, it is possible to output from the speaker 63 a clear voice having a reduced influence of noise.

Now a method of reducing noise based on the idea described above will be described.

Referring to the sound spectrum SP, noise profiles representing the frequency characteristic of noise caused by rotation of the rotating section 26 appear at a plurality of positions. However, the most conspicuous ones of frequencies of noise appearing in the sound spectrum SP are those appearing in the noise profile N1. Accordingly, a method of reducing noise corresponding to the noise profile N1 will be described hereinbelow, in which the description will be made separately for time point t1≤ti<t8 and time point t8≤ti≤t24.

(1) On Time Point t1≤ti<t8

FIG. 7 is an explanatory diagram for an action of the intercom board 60 at time point t1≤ti<t8.

At time point t1≤ti<t8, the rotating section 26 is not rotating yet (see FIG. 4), and therefore, no noise by rotation of the rotating section 26 is generated. Accordingly, an analog signal AS(ti) representing sound received at the microphone 61 at time point t1≤ti<t8 contains no noise by rotation of the rotating section 26.

The analog signal AS(ti) from the microphone 61 is input to the preamplifier 621. The preamplifier 621 amplifies the analog signal AS(ti) received from the microphone 61, and outputs an amplified analog signal AS(ti)_a to the ADC 622.

The ADC 622 converts the analog signal AS(ti)_a received from the preamplifier 621 into a digital signal DS(ti), and outputs it to the DSP 623.

On the other hand, the encoder 27 detects a rotation angle θ of the rotating section 26, and outputs a rotation angle signal RA representing the rotation angle θ to the TG control section 31. The TG control section 31 calculates a rotational speed vi of the rotating section 26 at time point ti based on the angle signal RA. A signal RV representing the calculated rotational speed vi is output to the DSP 623.

The DSP 623 sets a filter characteristic F(ti) for the DSP 623 at each time point ti (1≤i<8) based on the rotational speed vi. Specifically, the filter characteristic is set as below.

The DSP 623 first calculates a frequency f1(vi) to be removed using EQ. (2) for each time point ti (1≤i<8). Since the rotating section 26 is not rotating yet at time point t1≤ti<t8, vi=0 (rps). Therefore, substituting vi in EQ. (2) with vi=0, the frequency f1(vi) is calculated as below:

$$f1(vi=0) = 0.42*0$$
$$= 0 \text{ (kHz)}.$$

After determining the value of f1(vi), the DSP 623 sets the filter characteristic based on the value of f1(vi). Here, f1(vi) is calculated as f1(vi)=0. This f1(vi)=0 means that no noise by rotation of the rotating section 26 is generated, that is, no frequency to be removed has appeared yet. Therefore, the DSP 623 sets the filter characteristic for the DSP 623 to that with which no removal of the frequency of noise is applied. In FIG. 7 in its upper portion is schematically shown a filter characteristic F(ti) that the DSP 623 sets at time point t1≤ti<t8. Since no frequency to be removed (notch frequency) appears yet at time point t1≤ti<t8, the gain of the filter characteristic F(ti) has a value close to one. The filter characteristic for the DSP 623 is set to the filter characteristic F(ti) shown in FIG. 7.

Since the DSP 623 thus applies no removal of the frequency of noise to the frequencies contained in the digital signal DS(ti), it outputs a digital signal DS(ti)_f in which no removal of the frequency of noise is applied. The DAC 624 converts the digital signal DS(ti)_f output from the DSP 623 into an analog signal AS(ti)_f, and outputs it to the speaker amplifier 625. The speaker amplifier 625 amplifies the analog signal AS(ti)_f, and outputs the amplified analog signal to the speaker 63 as an output signal AO(ti). The speaker 63 generates sound corresponding to the output signal AO(ti) received from the speaker amplifier 625.

Figure 8:
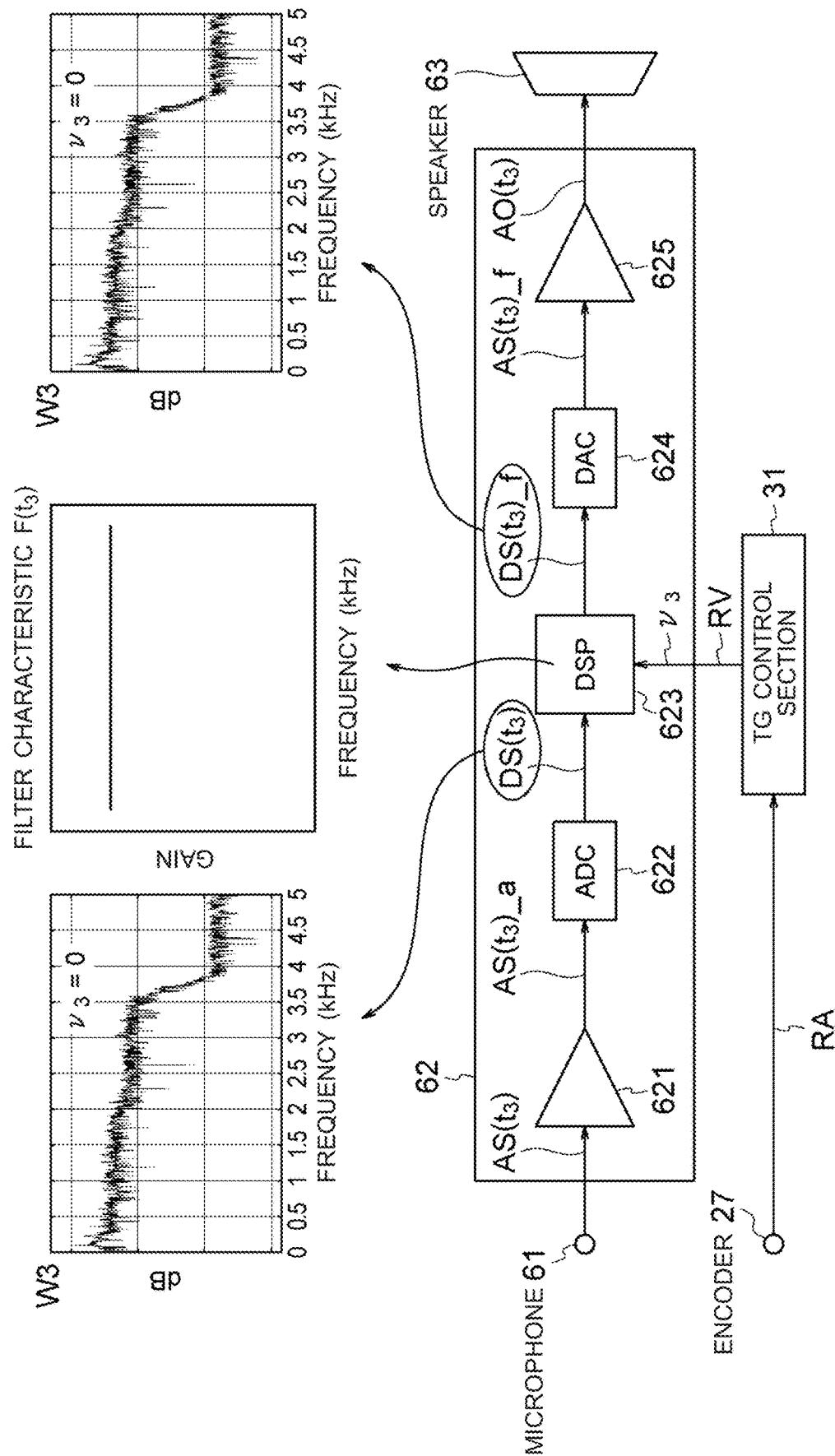
FIG. 8 An explanatory diagram for filter processing at time point t3.

Now for better understanding of the filter processing at time point t1≤ti<t8, let us consider filter processing at time point t3 as a concrete example. FIG. 8 is an explanatory diagram for filter processing at time point t3.

The analog signal AS(t3) from the microphone 61 is input to the preamplifier 621. The preamplifier 621 amplifies the analog signal AS(t3) received from the microphone 61, and outputs an amplified analog signal AS(t3)_a to the ADC 622.

The ADC 622 converts the analog signal AS(t3)_a received from the preamplifier 621 into a digital signal DS(t3), and outputs it to the DSP 623. FIG. 8 shows in its upper left a waveform representing the frequency characteristic of the sound pressure in the digital signal DS(t3).

On the other hand, the encoder 27 detects a rotation angle θ of the rotating section 26, and outputs a rotation angle signal RA representing the rotation angle θ to the TG control section 31. The TG control section 31 calculates a rotational speed v3 of the rotating section 26 at time point t3 based on the angle signal RA. A signal RV representing the calculated rotational speed v3 is output to the DSP 623.

The DSP 623 calculates a frequency f1($v$3) to be removed using EQ. (2). Since the rotating section 26 is not rotating yet at time point t3, $v$3=0 (rps). Therefore, substituting v3 in EQ. (2) with $v$3=0, the frequency f1($v$3) is calculated as f1($v$3)=0 (kHz).

After determining the value of f1($v$3), the DSP 623 sets the filter characteristic based on the value of f1($v$3). Since f1($v$3)=0, the DSP 623 sets the filter characteristic for the DSP 623 to a filter characteristic F(t3) with which no removal of the frequency of noise is applied.

Since the DSP 623 thus applies no removal of the frequency of noise to the frequencies contained in the digital signal DS(t3), it outputs a digital signal DS(t3)_f in which no removal of the frequency of noise is applied. FIG. 8 shows in its upper right a waveform representing the frequency characteristic of the sound pressure in the digital signal DS(t3)_f output from the DSP 623.

The digital signal DS(t3)_f output from the DSP 623 is converted into an analog signal AS(t3)_f by the DAC 624, and is output to the speaker amplifier 625. The speaker amplifier 625 amplifies the analog signal AS(t3)_f, and outputs the amplified analog signal to the speaker 63 as an output signal AO(t3). The speaker 63 generates sound corresponding to the output signal AO(t3) received from the speaker amplifier 625.

A signal at time point t1≤ti<t8 is processed as described above.

(2) On Time Point t8≤ti≤t24

Figure 9:
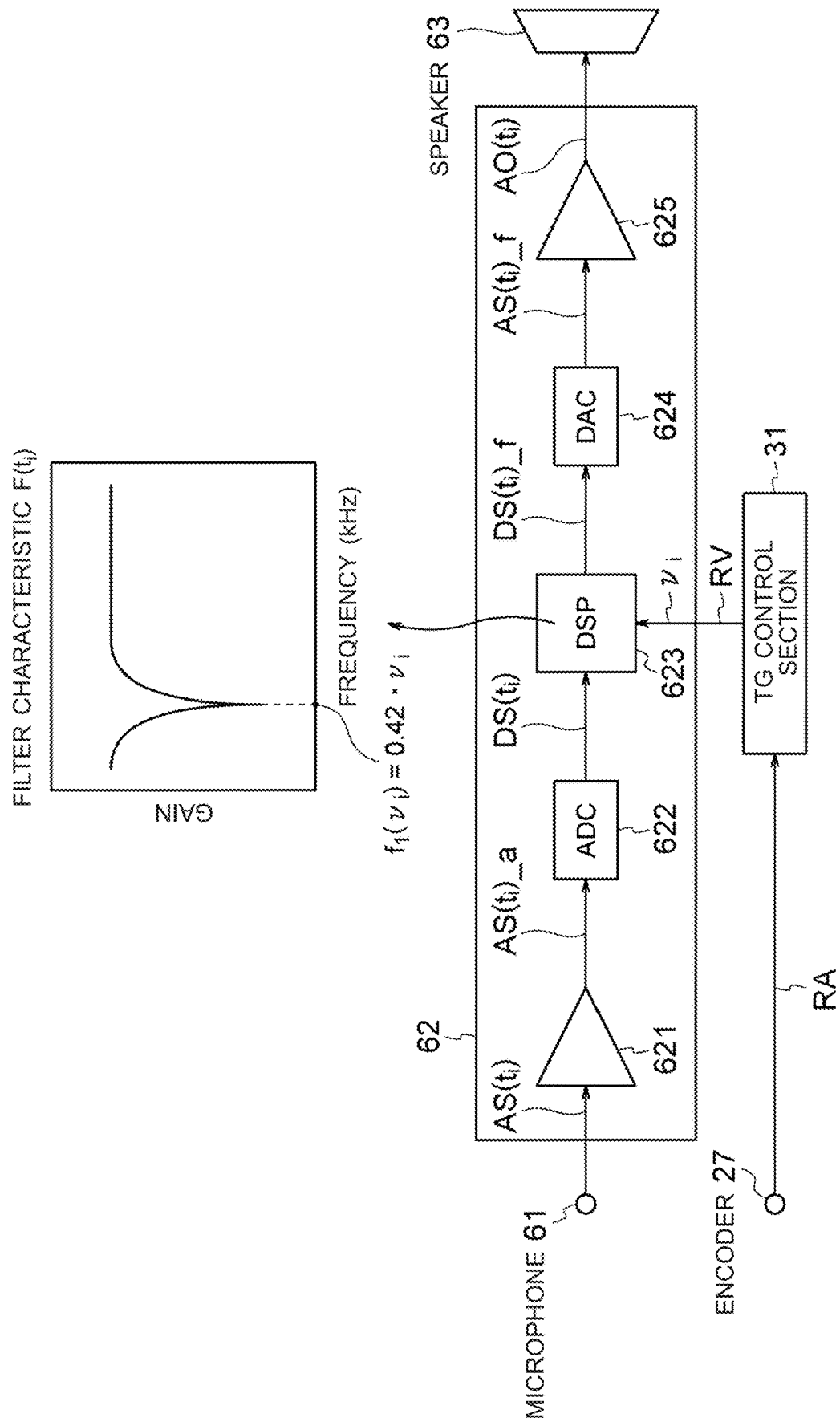
FIG. 9 An explanatory diagram for an action of the intercom board 60 at time point t8≤ti≤t24.

FIG. 9 is an explanatory diagram for an action of the intercom board 60 at time point t8≤ti≤t24.

At time point t8≤ti≤t24, the rotating section 26 is rotating (see FIG. 4). Therefore, an analog signal AS(ti) representing sound received at the microphone 61 at time point ti (8≤i≤24) contains noise by rotation of the rotating section 26.

The analog signal AS(ti) from the microphone 61 is amplified at the preamplifier 621. An amplified analog signal AS(ti)_a is converted into a digital signal DS(ti) at the ADC 622, and is output to the DSP 623.

On the other hand, the encoder 27 detects a rotation angle θ of the rotating section 26, and outputs a rotation angle signal RA representing the rotation angle θ to the TG control section 31. The TG control section 31 calculates a rotational speed vi of the rotating section 26 at time point ti based on the angle signal RA. A signal RV representing the calculated rotational speed vi is output to the DSP 623.

The DSP 623 sets a filter characteristic F(ti) for the DSP 623 at each time point ti (8≤i≤24) based on the rotational speed vi. Specifically, the filter characteristic F(ti) is set as below.

The DSP 623 first calculates a frequency f1($vi$) to be removed using EQ. (2) for each time point ti (8≤i<24). The frequency f1($vi$) is calculated as below:

$$f1(vi)=0.42*vi \text{ (kHz)}, \quad (2)'$$

where 8≤i≤24.

As shown in EQ. (2)', f1 is calculated as f1($vi$)=0.42*vi in a period between time points t8≤ti≤t24. After determining the value of f1($vi$), the DSP 623 sets a filter characteristic F(ti) based on the value of f1($vi$). FIG. 9 schematically shows in its upper portion the filter characteristic F(ti) in the case of f1($vi$)=0.42*vi. The filter characteristic F(ti) has such a characteristic that gain attenuates at notch frequency f1($vi$). It should be noted that the values of coefficients of a transfer function used in the DSP 623 may be adjusted to reduce or enhance the sharpness of attenuation of the filter characteristic F(ti).

The DSP 623 is set to have the filter characteristic F(ti) shown in FIG. 9 in a period between time points t8≤ti≤t24. Therefore, the DSP 623 applies removal of the frequency f1($vi$) of noise to the frequencies contained in the digital signal DS(ti), and outputs a digital signal DS(ti)_f in which f1($vi$) has been removed. The digital signal DS(ti)_f output from the DSP 623 is converted into an analog signal AS(ti)_f, and is output to the speaker amplifier 625. The speaker amplifier 625 amplifies the analog signal AS(ti)_f, and outputs the amplified analog signal to the speaker 63 as an output signal AO(ti). The speaker 63 generates sound corresponding to the output signal AO(ti) received from the speaker amplifier 625.

Therefore, in a period between time points t8≤ti≤t24, sound having reduced noise is output from the speaker 63. Thus, even when the subject makes a voice while the rotating section 26 is rotating, the operator can hear from the speaker 63 a clear voice having a reduced influence of noise.

Now for better understanding of the issue that noise can be reduced by the DSP 623 at time point t8≤ti≤t24, filter processing at time points t12, t16, t20, and t22 as representatives will be described.

(On Time Point t12)

Figure 10:
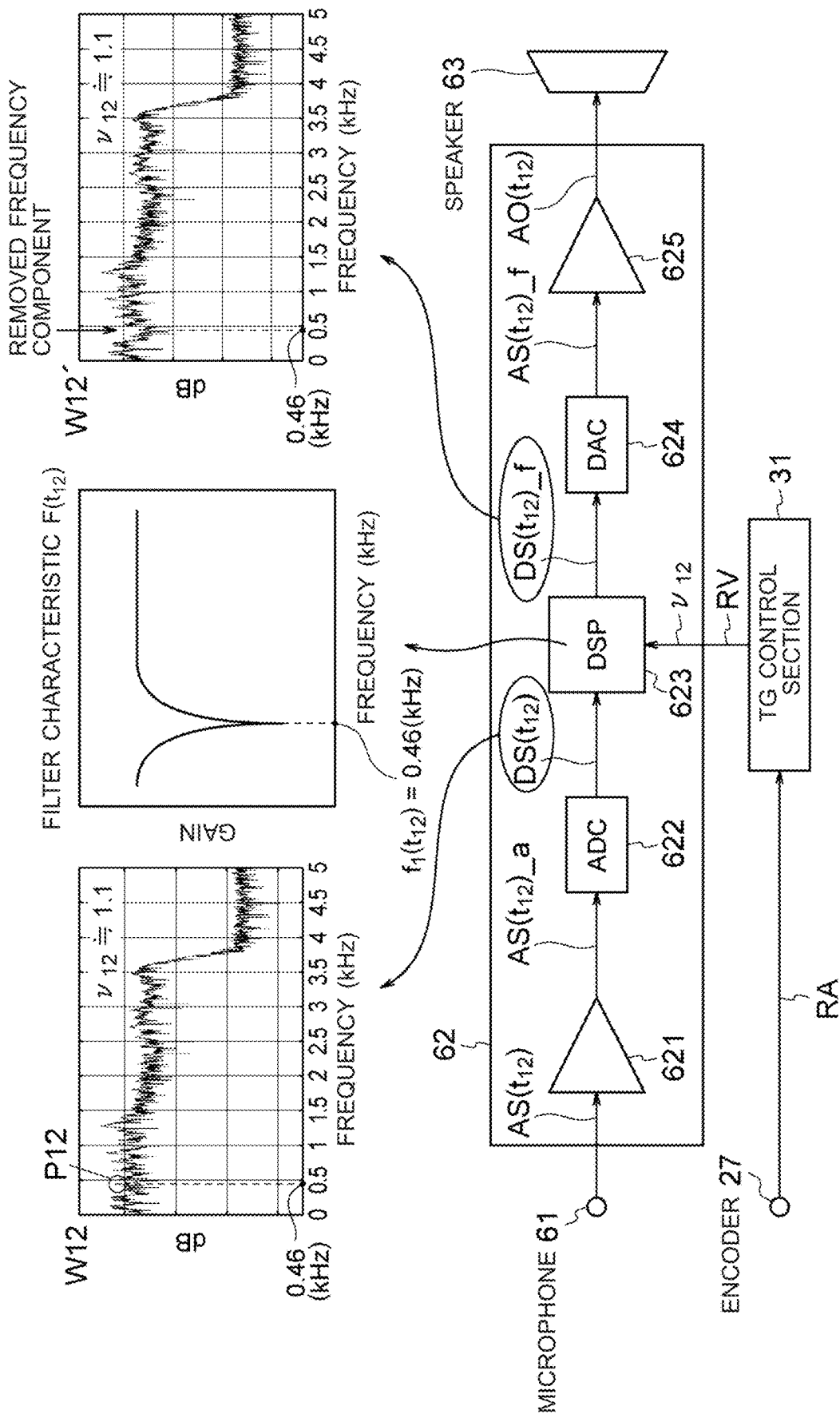
FIG. 10 An explanatory diagram for the filter processing at time point t12.

FIG. 10 is an explanatory diagram for filter processing at time point t12.

In FIG. 10 are shown a filter characteristic F(t12) of the DSP 623 at time point t12, and two waveforms w12 and w12'. The waveform w12 is a waveform representing a frequency characteristic of the sound pressure in a digital signal DS(t12) before being filter-processed, while the waveform w12' is a waveform representing a frequency characteristic of the sound pressure in a filter-processed digital signal DS(t12)_f.

Since the rotational speed v12 of the rotating element 26 is v12≈1.1 (rps) at time point t12, a frequency f1($v$12) is calculated as below:

$$f1(v12) = 0.42 * 1.1$$
$$= 0.46 \text{ (kHz)}.$$

Therefore, at time point t12, the DSP 623 is set to have a filter characteristic F(t12) with a notch frequency of f1($v$12)=0.46 (kHz), as shown in FIG. 10.

The DSP 623 applies removal of the frequency f1($v$12) of noise to the frequencies contained in the digital signal DS(t12), and outputs a digital signal DS(t12)_f in which f1($v$12) has been removed. Therefore, a frequency component of 0.46 (kHz) at point P12 can be removed from the waveform w12 at time point t12.

Since point P12 in the waveform w12 corresponds to point Q12 in the sound spectrum SP (see FIG. 6), removal of a frequency component in the waveform w12 at point P12 means removal of a frequency component at point Q12 in the sound spectrum SP.

The digital signal DS(t12) f output from the DSP 623 is converted into an analog signal AS(t12)_f, and is output to the speaker amplifier 625. The speaker amplifier 625 amplifies the analog signal AS(t12)_f, and outputs the amplified analog signal to the speaker 63 as an output signal AO(t12). The speaker 63 generates sound corresponding to the output signal AO(t12) received from the speaker amplifier 625.

Therefore, sound in which the frequency 0.46 (kHz) of noise has been removed is output to the speaker 63. Thus, even when the subject makes a voice while the rotating section 26 is rotating, the operator can hear from the speaker 63 a clear voice having a reduced influence of noise.

(On Time Point t16)

Figure 11:
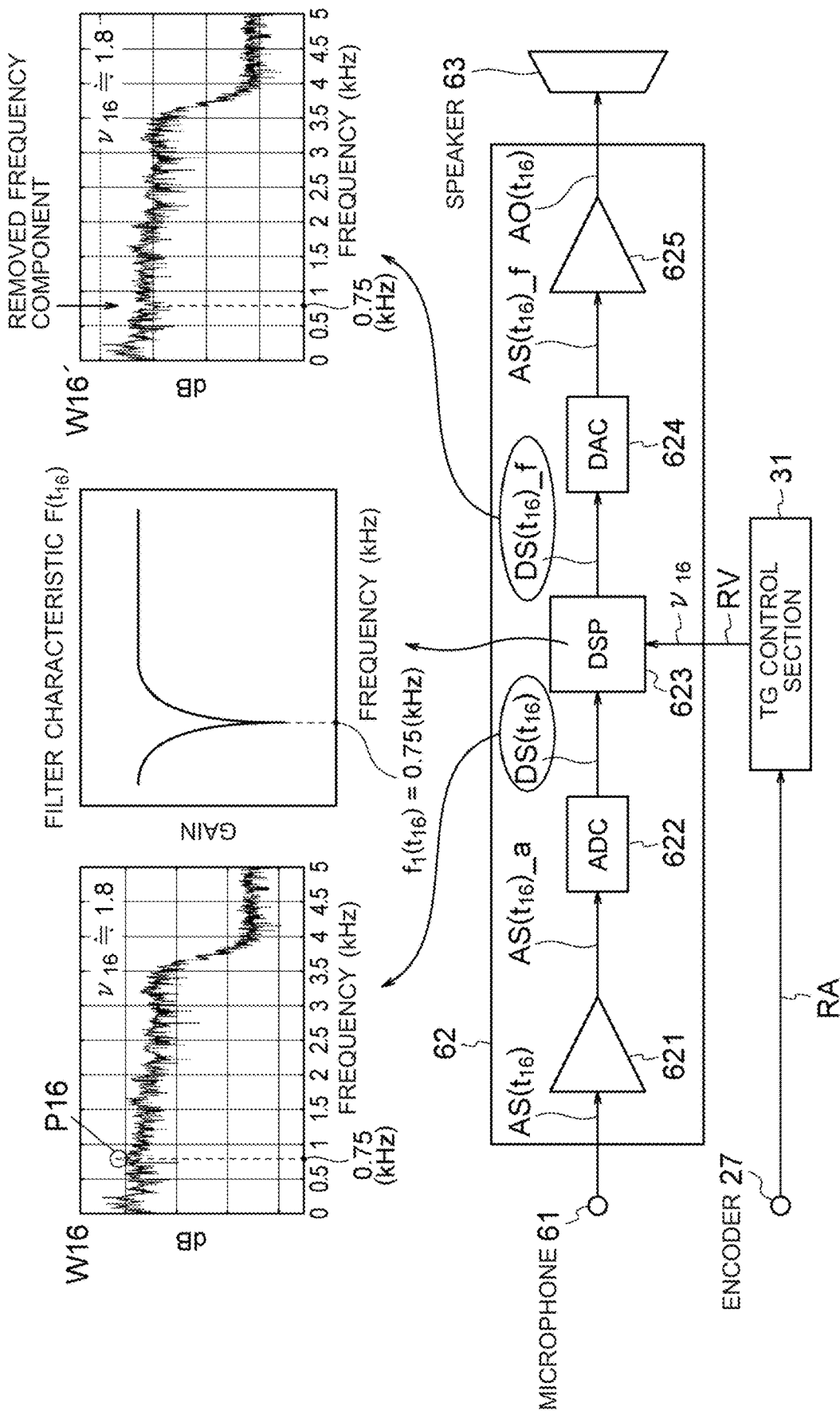
FIG. 11 An explanatory diagram for the filter processing at time point t16.

FIG. 11 is an explanatory diagram for filter processing at time point t16.

Since the rotational speed v16 of the rotating element 26 is v16≈1.8 (rps) at time point t16, a frequency f1(v16) is calculated as below:

$$f1(v16) = 0.42 * 1.8$$
$$= 0.75 \text{ (kHz)}.$$

Therefore, at time point t16, the DSP 623 is set to have a filter characteristic F(t16) with a notch frequency of f1(v16)=0.75 (kHz), as shown in FIG. 11.

The DSP 623 applies removal of the frequency f1(v16) of noise to the frequencies contained in the digital signal DS(t16), and outputs a digital signal DS(t16)_f in which f1(v16) has been removed. Therefore, a frequency component of 0.75 (kHz) at point P16 can be removed from the waveform w16 at time point t16.

Since point P16 in the waveform w16 corresponds to point Q16 in the sound spectrum SP (see FIG. 6), removal of a frequency component at point P16 in the waveform w16 means removal of a frequency component at point Q16 in the sound spectrum SP.

Therefore, sound in which the frequency 0.75 (kHz) of noise has been removed is output from the speaker 63. Thus, even when the subject makes a voice while the rotating section 26 is rotating, the operator can hear from the speaker 63 a clear voice having a reduced influence of noise.

(On Time Point t20)

Figure 12:
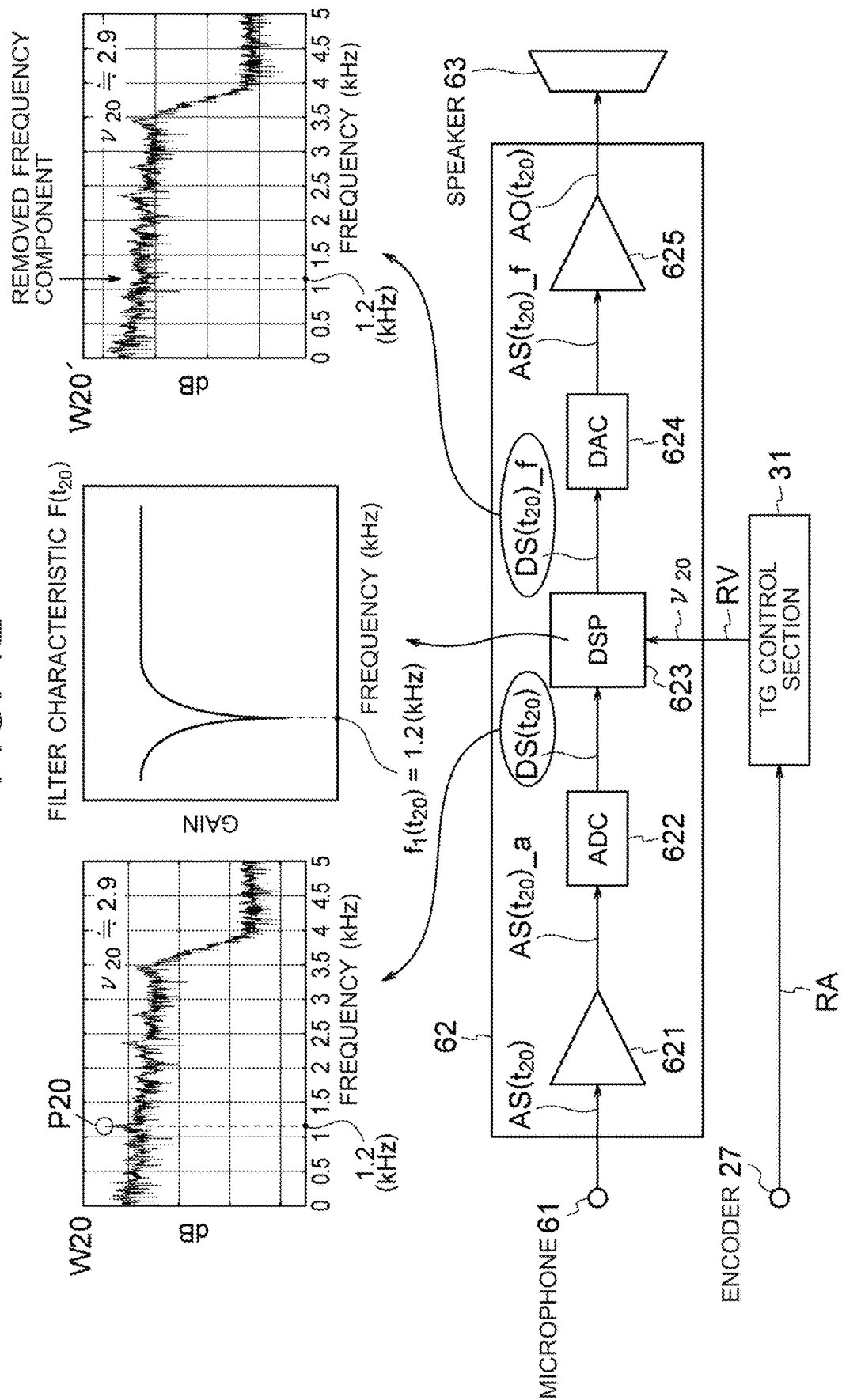
FIG. 12 An explanatory diagram for the filter processing at time point t20.

FIG. 12 is an explanatory diagram for filter processing at time point t20.

Since the rotational speed v20 of the rotating element 26 is v20≈2.9 (rps) at time point t20, a frequency f1(v20) is calculated as below:

$$f1(v20) = 0.42 * 2.9$$
$$= 1.2 \text{ (kHz)}.$$

Therefore, at time point t20, the DSP 623 is set to have a filter characteristic F(t20) with a notch frequency of f1(v20)=1.2 (kHz), as shown in FIG. 12.

A frequency component of 1.2 (kHz) at point P20 can thus be removed from the waveform w20 at time point t20.

Since point P20 in the waveform w20 corresponds to point Q20 in the sound spectrum SP (see FIG. 6), removal of a frequency component at point P20 in the waveform w20 means removal of a frequency component at point Q20 in the sound spectrum SP.

Therefore, sound in which the frequency 1.2 (kHz) of noise has been removed is output from the speaker 63. Thus, even when the subject makes a voice while the rotating section 26 is rotating, the operator can hear from the speaker 63 a clear voice having a reduced influence of noise.

(On Time Point t22)

Figure 13:
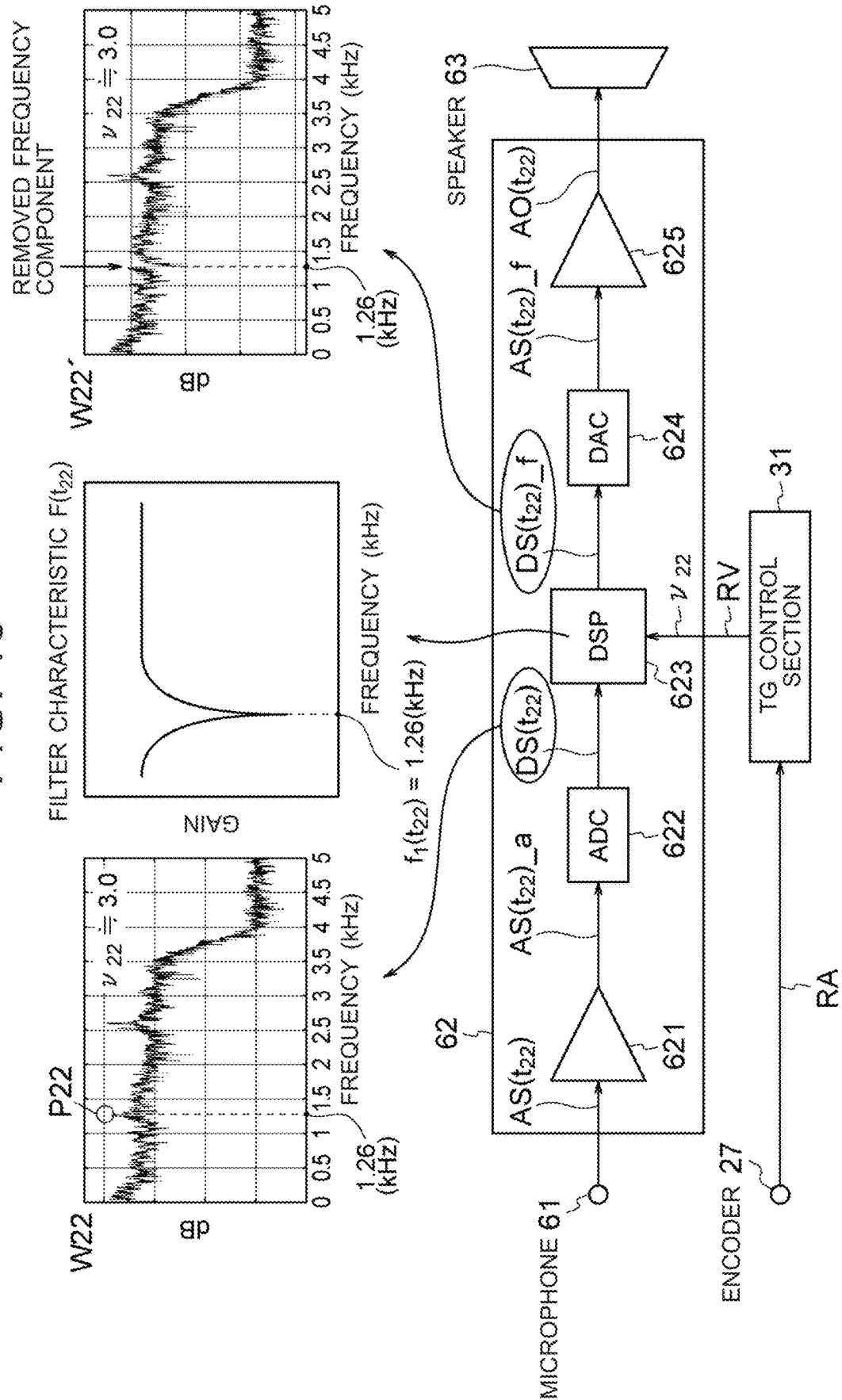
FIG. 13 An explanatory diagram for the filter processing at time point t22.

FIG. 13 is an explanatory diagram for filter processing at time point t22.

Since the rotational speed v22 of the rotating element 26 is v22≈3.0 (rps) at time point t22, a frequency f1(v22) is calculated as below.

$$f1(v22) = 0.42 * 3.0$$
$$= 1.26 \text{ (kHz)}.$$

Therefore, at time point t22, the DSP 623 is set to have a filter characteristic F(t22) with a notch frequency of f1(v22)=1.26 (kHz), as shown in FIG. 13.

A frequency component of 1.26 (kHz) at point P22 can thus be removed from the waveform w22 at time point t22.

Point P22 in the waveform w22 corresponds to point Q22 in the sound spectrum SP (see FIG. 6). Therefore, removal of the frequency component at point P22 in the waveform w22 means removal of the frequency component at point Q22 in the sound spectrum SP.

Therefore, sound in which the frequency 1.26 (kHz) of noise has been removed is output from the speaker 63. Thus, even when the subject makes a voice while the rotating section 26 is rotating, the operator can hear from the speaker 63 a clear voice having a reduced influence of noise.

In a period between time points t8≤ti≤t24, filter processing is executed as described above.

As described above, in the first embodiment, filter characteristics may be modified according to the rotational speed vi of the rotating section 26. Thus, the operator can hear from the speaker 63 a clear voice having a reduced influence of noise.

FIG. 14 is a diagram showing a sound spectrum SP un-filter-processed by the DSP and a sound spectrum SP' filter-processed by the DSP.

There appears in the un-filter-processed sound spectrum SP a noise profile N1 in which the frequency of noise shifts with time. It can be seen in the sound spectrum SP' obtained by filter-processing according to the method in the present embodiment, however, that the frequency components of the sound pressure in the noise profile N1 have been reduced. Therefore, it can be seen that in spite of the fact that the frequency at which the peak of the sound pressure of noise appears shifts depending upon the rotational speed vi of the rotating section 26, noise can be reduced because the DSP 623 is set to a filter characteristic F(ti) suitable to the rotational speed vi while the rotating section 26 is rotating.

In the first embodiment is described an example of execution of filter processing by focusing upon a case that the relationship between the rotational speed vi of the rotating section 26 and the frequency f1(vi) of noise is expressed as linear. However, the present invention is not limited to the case that the relationship between the rotational speed vi of the rotating section 26 and the frequency f1(vi) of noise is expressed as linear. The present invention may be applied to a case in which the relationship between the rotational speed vi of the rotating section 26 and the frequency f1(vi) of noise is expressed to be non-linear insofar as the frequency f1(vi) of noise can be identified with respect to the rotational speed vi of the rotating section 26.

(2) Second Embodiment

As compared with the first embodiment, a second embodiment is different therefrom in the method of setting the filter characteristic for the DSP 623, although it is the same as the first embodiment in other points. Therefore, in describing the second embodiment, the method of setting the filter characteristic for the DSP 623 will be mainly addressed.

In the first embodiment, EQ. (2) is used to calculate the notch frequency $f1(vi)$ to be removed. In the second embodiment, however, rather than determining the frequency $f1(vi)$ calculated by EQ. (2) as a notch frequency to be removed, the frequency $f1(vi)$ calculated by EQ. (2) is used to define a frequency range in which the notch frequency to be removed is expected to occur. Then, the notch frequency to be removed is determined from within the defined frequency range. Specifically, the notch frequency is determined as below.

Figure 15:
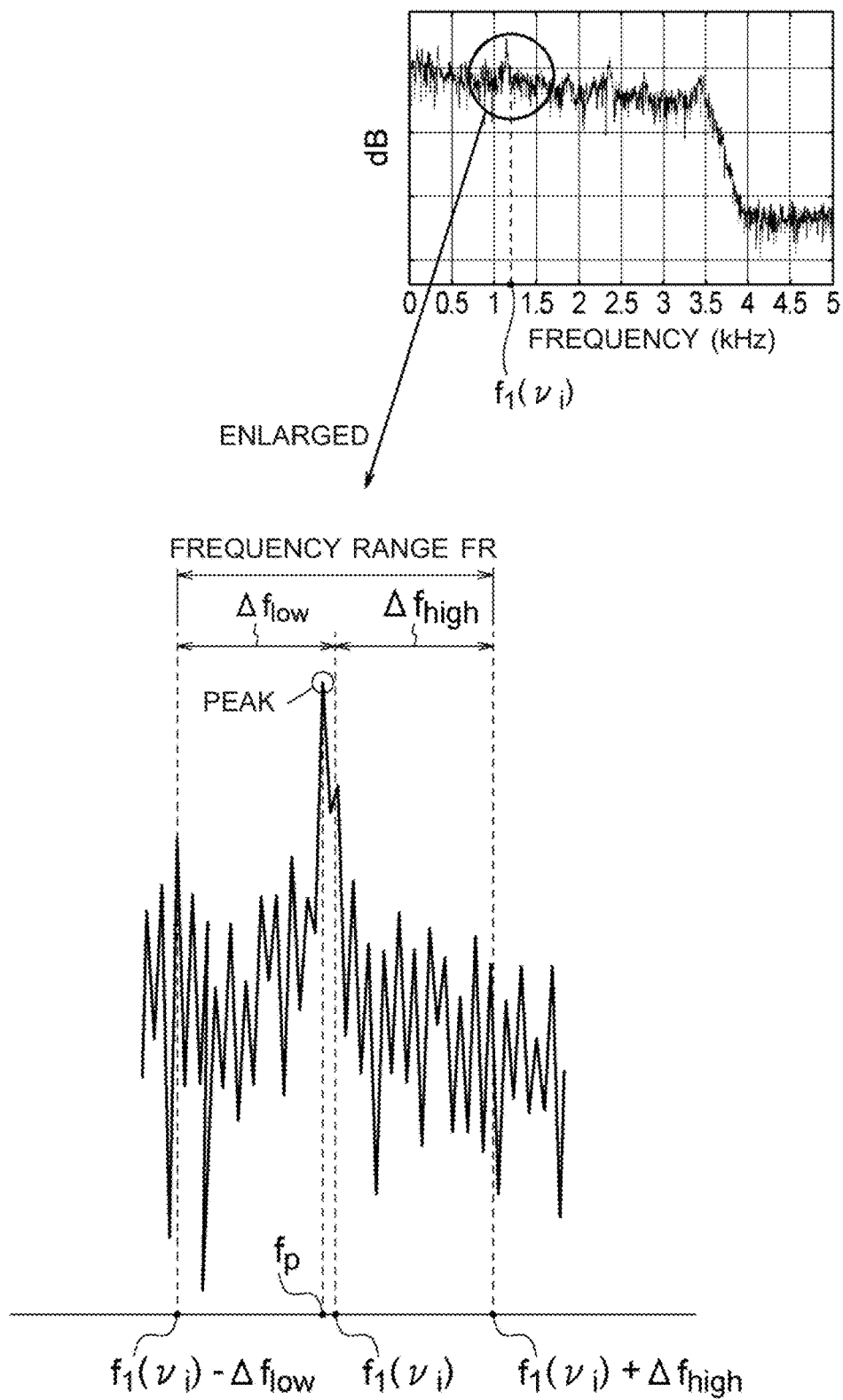
FIG. 15 An explanatory diagram for a filter characteristic setting method in a second embodiment.

FIG. 15 is an explanatory diagram for how to determine a notch frequency in the second embodiment.

First, the DSP 623 uses EQ. (2) to calculate $f1(vi)$.

Next, based on calculated $f1(vi)$, the DSP 623 defines a frequency range FR in which the notch frequency to be removed is expected to occur. Specifically, the DSP 623 defines frequency $f1(vi)-\Delta f_{low}$, which is a frequency shifted relative to the value of $f1(vi)$ by $\Delta f_{low}$ toward the lower frequency side, and frequency $f1(vi)+\Delta f_{high}$, which is a frequency shifted relative to the value of $f1(vi)$ by $\Delta f_{high}$ toward the higher frequency side, and defines a range of from $f1(vi)-\Delta f_{low}$ to $f1(vi)+\Delta f_{high}$ as the frequency range FR in which the notch frequency to be removed is expected to occur. Therefore, in the second embodiment, instead of being used as the notch frequency to be removed, the frequency $f1(vi)$ in EQ. (2) is used as a referential frequency serving as a basis for defining the frequency range FR in which the notch frequency to be removed is expected to occur.

The values of $\Delta f_{low}$ and $\Delta f_{high}$ are determined beforehand, and they can be determined, for example, with reference to the position of the frequency peak that actually appears in the sound spectrum. However, too small values of $\Delta f_{low}$ and $\Delta f_{high}$ may cause the notch frequency to be removed to fall outside the frequency range FR, while too large values of $\Delta f_{low}$ and $\Delta f_{high}$ result in too wide a frequency range FR so that frequencies at which the notch frequency to be removed obviously never appear also fall within in the frequency range FR, causing poorer efficiency in the detection processing. Therefore, it is desirable to set the values of $\Delta f_{low}$ and $\Delta f_{high}$ to as small a value as possible provided that the notch frequency to be removed does not fall outside the frequency range FR. The values of $\Delta f_{low}$ and $\Delta f_{high}$ may be set to values of the order of several hundred Hz, for example.

After defining the frequency range FR, the DSP 623 detects a frequency fp at which a maximum value (or peak) of the sound pressure appears from within the frequency range FR, and determines the detected frequency fp as a frequency fp of noise. For the detecting method, a known detecting technique may be used. After detecting the frequency fp of noise, the DSP 623 sets the filter characteristic for the DSP 623 to that for removing the detected frequency fp of noise.

It should be noted that the rotational speed is vi=0 when the rotating section 26 is not rotating, and accordingly, f1 is calculated as $f1(vi)=0$. Therefore, when f1 is calculated as $f1(vi)=0$, the DSP 623 may set the filter characteristic for the DSP 623 to that with which no removal of the frequency of noise is applied, similarly to the first embodiment.

In the second embodiment, a frequency range FR in which search for the frequency of noise is made is defined based on the rotational speed vi of the rotating section 26, and the frequency fp of noise is detected from within the frequency range FR. Therefore, in the case that an actual frequency fp of noise is offset from the frequency $f1(vi)$ calculated by EQ. (2), the frequency of noise can be fully reduced.

Moreover, $\Delta f_{low}$ and $\Delta f_{high}$ may be fixed values or variable values that can be modified depending upon the rotational speed vi of the rotating section 26. The variable values $\Delta f_{low}$ and $\Delta f_{high}$ that can be modified depending upon the rotational speed vi of the rotating section 26 enable definition of a frequency range suitable for the rotational speed vi of the rotating section 26.

The first and second embodiments focus upon the rotating section 26 rotating along the path 26a surrounding the bore portion 20 as a rotating section causing noise. However, it is possible to apply the present invention to a case that it is desired to reduce, in addition to noise caused by rotation of the rotating section 26, noise caused by rotation of any other rotating section (for example, the rotating section for rotating the anode of the X-ray tube 21) incorporated in the gantry, and/or noise caused by rotation of any rotating section (for example, that incorporated in the table) provided outside of the gantry.

Moreover, a DSP is used as the filter section in the first and second embodiments. However, the present invention is not limited to DSPs as the filter section insofar as noise can be reduced, and any other circuitry than the DSP, for example, FPGAs (field-programmable gate arrays) may be used as the filter section.

Furthermore, the first and second embodiments address a case in which the intercom apparatus 60 is used for the CT apparatus. However, the intercom apparatus in the present invention may be applied to any other medical apparatus than the CT apparatus that has a rotating section causing noise.

DESCRIPTION OF REFERENCE SYMBOLS

1 X-ray CT apparatus
2 Gantry
4 Table
5 Subject
7 Operation console
20 Bore portion
21 X-ray tube
22 Aperture
23 Collimator device
24 X-ray detector
25 Data acquisition system
26 Rotating section
27 Encoder
28 High-voltage power source
29 Aperture drive apparatus
30 Rotation drive apparatus
31 TG control section
41 Cradle
42 Drive apparatus
60 Communication apparatus
61 Microphone
62 Intercom board
63 Speaker
71 Input device
72 Display device
73 Storage device
74 Computational processing device
621 Preamplifier
622 ADC
623 DSP
624 DAC
625 Speaker amplifier

The invention claimed is:

1. A communication apparatus used in a medical apparatus comprising a rotating section, said communication apparatus having:
   a microphone for receiving, during rotation of said rotating section, sound containing a voice of a subject to be examined and noise caused by the rotation of said rotating section;
   a filter section for executing filter processing for reducing said noise contained in the sound received by said microphone, wherein said filter section determines a frequency of the noise caused by the rotation of said rotating section based on a rotational speed of said rotating section, and sets a filter characteristic for said filter section so that a frequency component of said noise contained in said sound is removed, wherein said filter section determines a frequency range for searching for a frequency of noise corresponding to said rotational speed from among frequencies contained in said sound based on the rotational speed of said rotating section, and detects a frequency of said noise from within said frequency range; and
   a speaker for outputting the sound from which the frequency component of said noise has been removed.

2. The communication apparatus as recited in claim 1, wherein:
   said filter section determines a frequency of the noise caused by rotation of said rotating section using a formula representing a relationship between the rotational speed of said rotating section and the frequency of the noise caused by rotation of said rotating section.

3. The communication apparatus as recited in claim 1, wherein:
   said filter section determines a referential frequency for determining said frequency range based on the rotational speed of said rotating section.

4. The communication apparatus as recited in claim 3, wherein:
   said filter section determines said referential frequency using a formula representing the relationship between the rotational speed of said rotating section and the frequency of the noise caused by rotation of said rotating section.

5. The communication apparatus as recited in claim 1, wherein:
   said microphone outputs an analog signal representing the sound received by said microphone,
   said communication apparatus comprises:
      a first amplifier for amplifying said analog signal; and
      an analog-to-digital converter for converting the analog signal amplified by said first amplifier into a digital signal, and
   said filter section executes said filter processing on said digital signal.

6. The communication apparatus as recited in claim 5, having:
   a digital-to-analog converter for converting said digital signal filter-processed by said filter section into an analog signal; and
   a second amplifier for amplifying the analog signal output by said digital-to-analog converter, wherein
   said speaker receives the analog signal amplified by said second amplifier, and outputs sound corresponding to the received analog signal.

7. The communication apparatus as recited in claim 1, wherein:
   said medical apparatus comprises a gantry having a bore portion through which the subject is carried, and
   said rotating section is included in said gantry.

8. The communication apparatus as recited in claim 7, wherein:
   said rotating section rotates along a path surrounding said bore portion in a plane orthogonal to a body axis of said subject, and
   said rotating section is provided with an X-ray tube, and a detector for detecting X-rays emitted from said X-ray tube.

9. A medical apparatus having the communication apparatus as recited in claim 1.

10. A non-transitory computer-readable storage medium storing one or more processor-executable instructions wherein said one or more instructions, when executed by said processor, causes acts to be performed comprising:
    receiving a signal representing a rotational speed of a rotating section of a medical apparatus;
    determining, based on said signal, a frequency of noise caused by rotation of said rotating section; and
    setting a filter characteristic for a filter section so that a frequency component of said noise contained in a sound is removed, wherein the filter section includes determining a frequency range for searching for a frequency of noise corresponding to a rotational speed from among frequencies contained in the sound based on the rotational speed of said rotating section, and detects a frequency of said noise from within said frequency range.

11. The non-transitory computer-readable storage medium as recited in claim 10, further including instructions to determine a referential frequency for determining said frequency range based on the rotational speed of said rotating section.

12. The non-transitory computer-readable storage medium as recited in claim 11, further including instructions to determine said referential frequency using a formula representing the relationship between the rotational speed of said rotating section and the frequency of the noise caused by rotation of said rotating section.

13. The non-transitory computer-readable storage medium as recited in claim 10, further including instructions to determine a frequency of the noise caused by rotation of said rotating section using a formula representing a relationship between the rotational speed of said rotating section and the frequency of the noise caused by rotation of said rotating section.

* * * * *